(12) United States Patent
Culiat

(10) Patent No.: US 8,877,176 B2
(45) Date of Patent: Nov. 4, 2014

(54) METHODS FOR PROMOTING WOUND HEALING AND MUSCLE REGENERATION WITH THE CELL SIGNALING PROTEIN NELL1

(75) Inventor: Cymbeline T. Culiat, Oak Ridge, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 239 days.

(21) Appl. No.: 13/029,189

(22) Filed: Feb. 17, 2011

(65) Prior Publication Data
US 2011/0250186 A1 Oct. 13, 2011

Related U.S. Application Data

(62) Division of application No. 12/238,882, filed on Sep. 26, 2008, now Pat. No. 7,910,542.

(60) Provisional application No. 60/976,023, filed on Sep. 28, 2007.

(51) Int. Cl.
*A01N 63/00* (2006.01)
*A61K 38/48* (2006.01)
*A61K 31/70* (2006.01)

(52) U.S. Cl.
CPC ............... *A61K 31/70* (2013.01); *A61K 38/486* (2013.01)
USPC ....................................... 424/93.21; 424/93.2

(58) Field of Classification Search
CPC ................................. C12N 15/86; A61K 48/00
USPC ............................................. 424/93.2, 93.21
See application file for complete search history.

(56) References Cited

U.S. PATENT DOCUMENTS

| | | | |
|---|---|---|---|
| 7,052,856 | B2 | 5/2006 | Ting |
| 2006/0025367 | A1 | 2/2006 | Simari |
| 2006/0053503 | A1 | 3/2006 | Culiat et al. |
| 2006/0111313 | A1 | 5/2006 | Ting |
| 2006/0228392 | A1 | 10/2006 | Ting |
| 2006/0292670 | A1 | 12/2006 | Ting et al. |
| 2007/0128697 | A1 | 6/2007 | Ting et al. |
| 2007/0134291 | A1 | 6/2007 | Ting et al. |
| 2009/0087415 | A1 | 4/2009 | Culiat |
| 2011/0236325 | A1 | 9/2011 | Culiat et al. |

FOREIGN PATENT DOCUMENTS

| | | |
|---|---|---|
| WO | 02/100426 | 12/2002 |
| WO | 2004024893 | 3/2004 |
| WO | 2004/072100 | 8/2004 |
| WO | 2006089023 | 8/2006 |
| WO | 2008073631 | 6/2008 |
| WO | 2008109274 | 9/2008 |
| WO | 2011091244 | 7/2011 |

OTHER PUBLICATIONS

Zhang et al., JCI, 2002, vol. 110, pp. 861-870.*
James et al., Biochemical and Biophysical Res. Comm., 2011, vol. 411, pp. 126-131.*
Narang et al., 2006, Pharmacological Reviews, vol. 58(2), pp. 194-243.*
Ekser et al, Oct. 21, 2011, The Lancet, pp. 1-12.*
Lin et al., 2009, Transplant Immunology, vol. 21, pp. 75-80.*
Strauer et al., 2003, Circulation, vol. 107, pp. 929-934.*
Li et al., J. Cerebral Blood Flow and Met., 2010, vol. 30, pp. 653-663.*
Yang et al. 2005, Cytotherapy, vol. 7(3), pp. 273-281.*
Kuroda et al., 1999, Biochemical and Biophysical Res. Comm., vol. 265, pp. 79-86.*
Trollet et al. (2009, Expert Opin. Ther., vol. 9(7), pp. 849-866).*
Naldini et al. (2011, Nat. Rev. Genetics, vol. 12, pp. 301-315).*
Raymond ed al. (Exp. Neurology, 1997, vol. 144, pp. 82-91).*
Prieto et al., (Gene Therapy, 2008, vol. 15, pp. 765-771).*
Hentze et al. (2009, Stem Cell Res., vol. 2, pp. 198-210).*
Norrman et al. (2010, PLoS One, vol. 5(8), pp. 1-10).*
Franke et al., "Systematic Association Mapping Identifies NELL1 as a Novel IBD Disease Gene," PLoS One, 2007, pp. 1-13, vol. 8(e691) and supplemental documents.
Aghaloo et al., "A Study of the Role of Nell-1 Gene Modified Goat Bone Marrow Stromal Cells in Promoting New Bone Formation," Molecular Therapy, 2007, pp. 1872-1880, vol. 15(10).
Liu et al., "Characterizing the Role of the Neill Gene in Cardiovascular Development," U.S. Department of Energy Journal of Undergraduate Research, 2007, pp. 63-70.
Liu, L.Y. et al., "Characterizing the Role of the Nell1 Gene in Cardiovascular Development" American Association for the Advancement of Science, San Francisco, CA, Presentation on Feb. 15-17, 2007 (Abstract).
Desai, J. et al. "Nell1, a Gene Coding for a Novel PKC-binding Protein is a Candidate for Late-Gestation Recessive Lethal Mutations at the I7R6 Locus" 16th International Mouse Genome Conference, San Antonio, TX, Presentation on Nov. 17-21, 2002 (Abstract).
Desai, J. et al., "Nell1-deficient Mice have Reduced Expression of Extracellular Matrix Proteins Causing Cranial and Vertebral Defects" 20th International Mouse Genome Conference, Charleston, SC, Presentation on Nov. 14, 2006 (Abstract).
Desai, J. et al., "Characterization of Mouse Nell1: A Gene Coding for a Novel PKC-binding Protein" Women in Science Meeting, ORNL, Oak Ridge, TN, Presentation on May 1, 2006 (Abstract).
Liu, L. et al., "Characterizing the Role of the Nell1 Gene in Cardiovascular Development" Oak Ridge Science Semester Poster Presentation. ORNL, Oak Ridge, TN, Presentation on Aug. 11, 2006 (Poster).

(Continued)

*Primary Examiner* — Anoop Singh
*Assistant Examiner* — David A Montanari
(74) *Attorney, Agent, or Firm* — Edna I. Gergel

(57) ABSTRACT

The present invention provides methods for promoting wound healing and treating muscle atrophy in a mammal in need. The method comprises administering to the mammal a Nell1 protein or a Nell1 nucleic acid molecule.

77 Claims, 8 Drawing Sheets

(56) References Cited

OTHER PUBLICATIONS

Tsutsumi, S. et al., "The Novel Gene Encoding a Putative Transmembrane Protein is Mutated in Gnathodiaphyseal Dysplasia (GDD)" American Journal of Human Genetics (2004) pp. 1255-1261, vol. 74.
Zhang, X., et al., "Nell-1 Induces Acrania-Like Cranioskeletal Deformities During Mouse Embryonic Development," Lab Invest (2006) pp. 633-644, vol. 86, Issue 7.
Zhang, X., et al., "Overexpression of Nell-1, a Craniosynostosis-Associated Gene, Induces Apoptosis in Osteoblasts During Craniofacial Development," J Bone Miner Res (2003) pp. 2126-2134, vol. 18, Issue 12.
Ting, K., et al., "Human NELL-1 Expressed in Unilateral Coronoal Synostosis," J Bone Miner Res (1999) pp. 80-89, vol. 14, Issue 1.
Aghaloo, T., et al., "Nell-1-Induced Bone Regeneration in Calvarial Defects," Am J Pathol (2006) pp. 903-915, vol. 169, Issue 3.
Zhang, X., et al., "Craniosynostosis in Transgenic Mice Overexpressing Nell-1," J Clin Invest (2002) pp. 861-870, vol. 110, Issue 6.
Cowan, C.M., et al., "Nell-1 Induced Bone Formation Within the Distracted Intermaxillary Suture," Bone (2006) pp. 48-58, vol. 38, Issue 1.
Desai, J., et al., "Nell1-Deficient Mice Have Reduced Expression of Extracellular Matrix Proteins Causing Cranial and Vertebral Defects," Hum Mol. Genet (2006) pp. 1329-1341, vol. 15, Issue 8.
Maeda, K. et al., "Brain Specific Human Genes, NELL1 and NELL2, are Predominantly Expressed in Neuroblastoma and Other Embryonal Neuroephithelial Tumors," Neurol Med Chir (Tokyo) (2001) pp. 582-588, vol. 41, Issue 12.
Luce, M.J., et al., "The Neuronal EGF-related genes NELL1 and NELL2 are Expressed in Hemopoietic Cells and Developmentally Regulated in the B Lineage," Gene (1999) pp. 121-126, vol. 231, Issue 1-2.
Kuroda, S. et al., "Biochemical Characterization and Expression Analysis of Neural Thrombospondin-1-like Proteins NELL1 and NELL2," Biochem Biophys Res Commun (1999) pp. 79-86, vol. 265, Issue 1.
Watanabe, T.K., et al., "Cloning and Characterization of Two Novel Human cDNAs (NELL1 and NELL2) Encoding Proteins with Six EGF-Like Repeats," Genomics (1996) pp. 273-276, vol. 38.
Shen, Y., et al., "Knock Down of NELL2 in Wilms' Tumor Cell Line," Journal of the William Jarvie Society (2006) p. 41, vol. 49, Abstract.
Santini, M. P. et al., "Signalling Pathways in Cardiac Rengeneration," Novartis Found Symp (2006) pp. 228-243, vol. 274.
Rubartt, M., et al., "Cell-Based Approaches for Cardiac Repair," Ann NY Acad Sci (2006) pp. 34-38, vol. 1080.
Ott, H.C., et al.., "From Cardiac Repair to Cardiac Regeneration-Ready to Translate?," Expert Opin Biol Ther. (2006) pp. 867-878, vol. 6, Issue 9.
Rosenthal, N., et al., "Growth Factor Enhancement of Cardiac Regeneration," Cell Transplant. 15 (Suppl 1): S41-S45 (2006).
Kuroda, S., et al., "Involvement of Epidermal Growth Factor-Like Domain of NELL Proteins in the Novel Protein-Protein Interaction with Protein Kinase C," Biochem Biophys Res Commun (1999) pp. 752-757, vol. 265, Issue 3.
Haider, H.K.H., "Bone Marrow Cells for Cardiac Regeneration and Repair: Current Status and Issues," Expert Rev Cardiovasc Ther. (2006) pp. 557-568, vol. 4, Issue 4.
Orlic, D., et al., "Transplanted Adult Bone Marrow Cells Repair Myocardial Infarcts in Mice," Ann NY Acad Sci (2001) pp. 221-230, vol. 938, Issue 1.
Lu, S.S., et al., "The Osteoinductive Properties of Nell-1 in a Rat Spinal Fusion Model," The Spine Journal (2007) pp. 50-60, vol. 7, Issue 1.
The Reporter, No. 78 (Jun. 2006), published by Oak Ridge National Laboratory, accessible on line at http:://www.ornl.gov/info/reporter/no78/June06 dw.htm.
Liu, L., et al., Characterizing the role of the Nell1 Gene in Cardiovascular Development, U.S. Department of Energy Journal of Undergraduate Research, 2007 (Abstract).
Diwan, AD., et al., "Current Concepts in Interverterbral Disk Restoration," Orthopedic Clinics of North America (2000) pp. 453-464, vol. 31, No. 3.
Rinchik, E.M., et al., "Functional Annotation of Mammalian Genomic DNA Sequence by Chemical Mutagenesis: A Fine-Structure Genetic Mutation Map of a 1-to 2-cM Segment of Mouse Chromosome 7 Corresponding to Human Chromosome 11p14p15," PNAS (2002) pp. 844-849, vol. 99, Issue 2.
Culiat, C.T., et al., Nell1: A Candidate Gene for ENU-Induced Recessive Lethal Mutations at the 17R6 Locus and Potential Mouse Models for Human neonatal Unilateral . . . ,: International Mammalian Genome Society, 15th International Mouse Genome Conference (2001).
Culiat, CT., et al., "Nell1: A Candidate Gene for ENU-Induced Recessive Lethal Mutations at the 17R6 Locus and Potential Mouse Models for Human Neonatal Unilateral Coronal Synostosis (UCS)," Jan. 27-31, 2002 (abstract).
Baraggi, R., et al., "Protein Kinase C (PKC) Isoenzymes Exhibit Specific Expression in the Vertebral Column of Human Fetuses," J. Biol. Res. (1995) pp. 83-91, LXXI.
Yomamoto, et al., "Regulation of Bone Morphogenetic Proteins in Early Embryonic Development," Naturwussenschaften (2004) pp. 519-534, vol. 91.
Cowan, et al., "Synergistic Effects of Nell-1 and BMP-2 on the Osteogenic Differentiation of Myoblasts." J. Bone Mineral Res. (2007) pp. 918-930, vol. 22.
Schmitt, et al., "BMP2 Initiates Chondrogenlc Lineage Development of Adult Human Mesenchymal Stem Cells in High-Density Culture," Differentiation (2003) pp. 567-577, vol. 71, Issue 9-10.
Pettit, et al., "The Development of Site-Specific Drug-Delivery Systems for Protein and Peptide Biopharmaceuticals" Trends in Biotechnology (1998) pp. 343-349, vol. 16.
Wells, J.A. "Additivity of Mutational Effects in Proteins" Biochemistry (1990) pp. 8509-8517, vol. 29(37).
Ngo, et al., "Computational complexity, protein structure prediction, and the Levinthal paradox" in Merz and La Grand (Eds.) The Protein Folding Problem and Tertiary Structure Prediction. Birkhauser: Boston (1994) pp. 491-495.

* cited by examiner

Figure 1

```
  1  mpmdlilvvw  fcvctartvv  gfgmdpdlqm  divteldlvn  ttlgvaqvsg  mhnaskaflf
 61  qdiereihaa  phvsekliql  frnkseftil  atvqqkpsts  gvilsirele  hsyfelessg
121  lrdeiryhyi  hngkprteal  pyrmadgqwh  kvalsvsash  lllhvdcnri  yervidppdt
181  nlppginlwl  gqrnqkhglf  kgiiqdgkii  fmpngyitqc  pnlnhtcptc  sdflslvqgi
241  mdlqellakm  taklnyaetr  lsqlenchce  ktcqvsglly  rdqdswvdgd  hcrnctcksg
301  avecrrmscp  plncspdslp  vhiagqcckv  crpkciyggk  vlaeggrilt  kscrecrggv
361  lvkitemcpp  lncsekdhil  pengccrvcr  ghnfcaegpk  cgensecknw  ntkatcecks
421  gyisvqgdsa  yceedidecaa  kmhychantv  cvnlpglyrc  dcvpgyirvd  dfsctehdec
481  gsgqhncden  aictntvqgh  sctckpgyvg  ngticrafce  egcryggtcv  apnkcvcpsg
541  ftgshceekdi  decsegiiec  hnhsrcvnlp  gwyhceecrsg  fhddgtysls  gescididec
601  alrthtcwnd  sacinlaggf  dclcpsgpsc  sgdcpheggl  khngqvwtlk  edrcsvcsck
661  dgkifcrrta  cdcqnpsadl  fccpecdtrv  tsqcldqngh  klyrsgdnwt  hscqgcrcle
721  gevdcwpltc  pnlsceytai  legeccprcv  sdpcladnit  ydirktclds  ygvsrlsgsv
781  wtmagspctt  ckckngrvcc  svdfeclqnn
```

Figure 2

```
   1 ggcgctgccg agccacctcc cccgccgccc gctagcaagt ttggcggctc caagccaggc
  61 gcgcctcagg atccaggctc atttgcttcc acctagcttc ggtgcccect gctaggcggg
 121 gaccctcgag agcgatgccg atggatttga ttttagttgt gtggttctgt gtgtgcactg
 181 ccaggacagt ggtgggcttt gggatggacc ctgaccttca gatggatatc gtcaccgagc
 241 ttgaccttgt gaacaccacc cttggagttg ctcaggtgtc tggaatgcac aatgccagca
 301 aagcattttt attcaagac atagaagag gatccatgc agctcctcat gtgagtgaga
 361 aattaattca gctgttccag aacaagagtg aattcaccat tttggccact gtacagcaga
 481 tggagagcag tggcctgagg gatgagattc ggtatcacta catacacaat gggaagccaa
 541 ggacagaggc acttccttac cgcatggcag atggacaatg cacaaggtt gcactgtcag
 601 ttagcgcctc tcatctcctg ctccatgtcg actgtaacag gatttatgag cgtgtgatag
 661 accctccaga taccaacctt cccccaggaa tcaatttatg gcttggccag cgcaaccaaa
 721 agcatggctt attcaaaggg atcatccaag atgggaagat catctttatg ccgaatggat
 781 atataacaca gtgtccaaat ctaaatcaca cttgcccaac ctgcagtgat ttcttaagcc
 841 tggtgcaagg aataatggat ttacaagagc ttttggccaa gatgactgca aaactaaatt
 901 atgcagagac aagacttagt caattggaaa actgtcattg tgagaagact tgtcaagtga
 961 gtggactgct ctatcgagat caagactctt gggtagatgg tgaccattgc aggaactgca
1021 cttgcaaaag tggtgccgtg aatgccgaa ggatgtcctg tccccctctc aattgctccc
1081 cagactccct cccagtgcac attgctggcc agtgctgtaa ggtctgccga ccaaaatgta
1141 tctatgcagg aaaagttctt gcagaaggcc agcggatttt aaccaagagc tgtcgggaat
1201 gccgaggtgg agttttagta aaaattacag aaatgtgtcc tccttcgaac tgctcagaaa
1261 aggatcacat tcttcctgag aatcagtgct gccgtgtctg tagaggtcat aacttttgtg
1321 cagaaggacc taaatgtggt gaaaactcag agtgcaaaaa ctggaataca aaagctactt
1381 gtgagtgcaa gagtggttac atctctgtcc agggagactc tgcctactgt gaagatattg
1441 atgagtgtgc agctaagatg cattactgtc atgccaatac tgtgtgtgtc aaccttcctg
1501 ggttatatcg ctgtgactgt gtcccaggat acattcgtgt ggatgacttc tcttgtacag
1561 aaacgatga atgtggcagc ggccagcaca ctgtgatga gaatgccatc tgcaccaaca
1621 ctgtccaggg acacagctgc acctgcaaac cgggctacgt ggggaacggg accatctgca
1681 gagctttctg tgaagagggc tgcagatacg gtggaacgtg tgtggctccc aacaaatgtg
1741 tctgtccatc tggattcaca ggaagccact gcgagaaaga tattgatgaa tgttcagagg
1801 gaatcattga gtgccacaac cattcccgct gcgttaacct gccaggtgg taccactgtg
1861 agtgcagaag cggtttccat gacgatggga cctattcact gtccggggag tcctgtattg
1921 acattgatga atgtgcctta agaactcaca cctgttggaa cgattctgcc tgcatcaacc
1981 tggcaggggg ttttgactgt ctctgcccct ctgggccctc ctgctctggt gactgtcctc
2041 atgaagggg gctgaagcac aatggccagg tgtggacctt gaaagaagac aggtgttctg
2101 tctgctcctg caaggatggc aagatattct gccgacggac agcttgtgat tgccagaatc
2161 caagtgctga cctattctgt gcccagaat gtgacaccag agtcacaagt caatgtttag
2221 accaaaatgg tcacaagctg tatcgaagtg gagacaattg gacccatagc tgtcagcagt
2281 gtcggtgtct ggaaggagag gtagattgct ggccactcac ttgccccaac ttgagctgtg
2341 agtatacagc tatcttagaa ggggaatgtt gtccccgctg tgtcagtgac cctgcctag
2401 ctgataacat cacctatgac atcagaaaaa cttgcctgga cagctatggt gtttcacggc
2461 ttagtggctc agtgtggacg atggctggat ctccctgcac aacctgtaaa tgcaagaatg
2521 gaagagtctg ttgttctgtg gattttgagt gtcttcaaaa taattgaagt atttacagtg
2581 gactcaacgc agaagaatgg acgaaatgac catccaacgt gattaaggat aggaatcggt
2641 agtttggttt ttttgtttgt tttgtttttt taaccacaga taattgccaa agtttccacc
2701 tgaggacggt gtttggaggt tgcctttgg acctaccact ttgctcattc ttgctaacct
2761 agtctaggtg acctacagtg ccgtgcattt aagtcaatgg ttgttaaaag aagtttcccg
2821 tgttgtaaat catgtttccc ttatcagatc attgcaaat acatttaaat gatctcatgg
2881 taaatgttga tgtatttttt ggtttatttt gtgtactaac ataatagaga gagactcagc
2941 tccttttatt tattttgttg atttatggat caaattctaa aataagttg cctgttgtga
3001 aaaaaaaaaa aaaaaaaaaa aaaaaa
```

Figure 3

```
  1 mpmdvilvlw fcvctartvl gfgmdpdlql diiseldlvn ttlgvtqvag lhnaskaflf
 61 qdvqreihsa phvsekliql frnkseftfl atvqqkpsts gvilsirele hsyfelessg
121 preeiryhyi hggkprteal pyrmadgqwh kvalsvsash lllhidcnri yervidppet
181 nlppgsnlwl gqrnqkhgff kgiiqdgkii fmpngfitqc pnlnrtcptc sdflslvqgi
241 mdlqellakm taklnyaetr lgqlenchce ktcqvsglly rdqdswvdgd ncgnctcksg
301 avecrrmscp plncspdslp vhisgqcckv crpkciyggk vlaeqqrilt ktcrecrggv
361 lvkiteacpp lncsakdhil penqccrvcp ghnfcaeapk cgensecknw ntkatceckn
421 gyisvqgnsa ycedidecaa kmhychantv cvnlpglyrc dcvpgyirvd dfsctehddc
481 gsgqhncdkn aictntvqgh sctcqpgyvg ngtickafce egcryggtcv apnkcvcpsg
541 ftgshcekdi decaegfvec hnysrcvnlp gwyhcecrsg fhddgtysls gescididec
601 alrthtcwnd sacinlaggf dclcpsgpsc sgdcpheggl khngqvwilr edrcsvcsck
661 dgkifcrrta cdcqnpnvdl fccpecdtrv tsqcldqsgq klyrsgdnwt hscqqcrcle
721 geadcwplac pslgceytam fegeccprcv sdpclagnia ydirktclds fgvsrlsgav
781 wtmagspctt ckckngrvcc svdlecienn
```

Figure 4

```
   1 aagcactggt ttcttgttag cgttggtgcg ccctgcttgg cggggttct ccggagcgat
  61 gccgatggat gtgattttag ttttgtggtt ctgtgtatgc accgccagga cagtgttggg
 121 ctttgggatg gaccctgacc ttcagctgga catcatctca gagctcgacc tggtgaacac
 181 caccctggga gtcacgcagg tggctggact gcacaacgcc agtaaagcat ttctatttca
 241 agatgtacag agagagatcc attcggcccc tcacgtgagt gagaagctga tccagctatt
 301 ccggaataag agcgagttca ccttttttggc tacagtgcag cagaaaccat ccacctcagg
 361 ggtgatactg tccatccggg agctggagca cagctatttt gaactggaga gcagtggccc
 421 aagagaagag atacgctacc attacataca tggtggaaag cccaggactg aggcccttcc
 481 ctaccgcatg gcagacggac aatggcacaa ggtcgcgctg tcagtgagcg cctctcacct
 541 cctgctccac atcgactgca ataggattta cgagcgtgtg atagaccctc cggagaccaa
 601 ccttcctcca ggaagcaatc tgtggcttgg gcaacgtaac caaaagcatg gcttttcaa
 661 aggaatcatc caagatggta agatcatctt catgccgaat ggtttcatca cacagtgtcc
 721 caacctcaat cgcacttgcc caacatgcag tgacttcctg agcctggttc aaggaataat
 781 ggatttgcaa gagcttttgg ccaagatgac tgcaaaactg aattatgcag agacgagact
 841 tggtcaactg gaaaattgcc actgtgagaa gacctgccaa gtgagtgggc tgctctacag
 901 ggaccaagac tcctgggtgg atggtgacaa ctgtgggaac tgcacgtgca aaagtggtgc
 961 cgtggagtgc cgcaggatgt cctgtccccc gctcaactgt ccccggact cacttcctgt
1021 gcacatttcc ggccagtgtt gtaaagtttg cagaccaaaa tgtatctatg gaggaaaagt
1081 tcttgctgag ggccagcgga ttttaaccaa gacctgccgg gaatgtcgag gtggagtctt
1141 ggtaaaaatc acagaagctt gccctccttt gaactgctca gcaaggatc atattcttcc
1201 agagaatcag tgctgcaggg tctgcccagg tcataacttc tgtgcagaag cacctaagtg
1261 cggagaaaac tcggaatgca aaattggaa tacaaaagca acctgtgagt gcaagaatgg
1321 atacatctct gtccagggca actctgcata ctgtgaagat attgatgagt gtgcagctaa
1381 aatgcactat tgtcatgcca acaccgtgtg tgtcaacttg ccggggttgt atcgctgtga
1441 ctgcgtccca gggtacatcc gtgtggatga cttctcttgt acggagcatg atgattgtgg
1501 cagcggacaa cacaactgcg acaaaaatgc catctgtacc aacacagtcc agggacacag
1561 ctgcacctgc cagccgggtt acgtgggaaa tggcaccatc tgcaaagcat tctgtgaaga
1621 gggttgcaga tacgaggta cctgtgtggc tcctaacaag tgtgtctgtc cttctggatt
1681 cacgggaagc cactgtgaga agatattga tgaatgcgca gagggattcg ttgaatgcca
1741 caactactcc cgctgtgtta acctgccagg gtggtaccac tgtgagtgca gaagcggttt
1801 ccatgacgat gggacctact cactgtccgg ggagtcctgc attgatatcg atgaatgtgc
1861 cttaagaact cacacttgtt ggaatgactc tgcctgcatc aacttagcag gaggatttga
1921 ctgcctgtgt ccctctgggc cctcctgctc tggtgactgt ccccacgaag gagggctgaa
1981 gcataatggg caggtgtgga ttctgagaga agacaggtgt tcagtctgtt cctgcaagga
2041 tgggaagata ttctgccggc ggacagcttg tgattgccag aatccaaatg ttgacctttt
2101 ttgctgccca gagtgcgata ccaggtcac cagccaatgt ttagatcaaa gtggacagaa
2161 gctctatcga agtggagaca actggaccca cagctgccag cagtgccgat gtctggaagg
2221 agaggcagac tgctggcctc tggcttgccc tagtttgggc tgtgaataca cagccatgtt
2281 tgaaggggag tgttgtcccc gatgtgtcag tgacccctgc ctggctggta atattgccta
2341 tgacatcaga aaaacttgcc tggacagctt tggtgtttcg aggctgagcg gagccgtgtg
2401 gacaatggct ggatctcctt gtacaacctg caaatgcaag aatgggagag tctgctgctc
2461 tgtggatctg gagtgtattg agaataactg aagattttaa atggactcgt cacgtgagaa
2521 aatgggcaaa atgatcatcc cacctgagga agaagagggg ctgattctt tttcttttta
2581 accacagtca attaccaaag tctccatctg aggaaggcgt ttggattgcc tttgccactt
2641 tgctcatcct tgctgaccta gtctagatgc ctgcagtacc gtgcatttcg gtcgatggtt
2701 gttgagtctc agtgttgtaa atcgcatttc cctcgtcaga tcatttacag atacatttaa
2761 aggggttcca tgataaatgt taatgtaact tttgtttatt ttgtgtactg acataataga
2821 gacttggcac catttatttta tttttcttga ttttggatc aaattctaaa aataaagttg
2881 cctgttgcga aaaaaaaaaa aaaaaaaaa aaaaa
```

Figure 5

```
  1  mpmdvilvlw fcvctartvl gfgmdpdlqm diiteldlvn ttlgvtqvag lhnaskaflf
 61  qdvqreihsa phvsekliql frnkseftfl atvqqkpsts gvilsirele hsyfelessg
121  preeiryhyi hggkprteal pyrmadgqwh kvalsvsash lllhvdcnri yervidppet
181  nlppgsnlwl gqrnqkhgff kgiiqdgkii fmpngfitqc pnlnrtcptc sdflslvqgi
241  mdlqellakm taklnyaetr lgqlenchce ktcqvsglly rdqdswvdgd ncrnctcksg
301  avecrrmscp plncspdslp vhisgqcckv crpkciyggk vlaeggrilt ktcrecrggv
361  lvkiteacpp lncsekdhil penqccrvcr ghnfcaeapk cgensecknw ntkatceckn
421  gyisvqgnsa ycedidecaa kmhychantv cvnlpglyrc dcipgyirvd dfsctehddc
481  gsgqhncdkn aictntvqgh sctcqpgyvg ngtvckafce egcryggtcv apnkcvcpsg
541  ftgshcekdi decaegfvec hnhsrcvnlp gwyhcecrsg fhddgtysls gescididec
601  alrthtcwnd sacinlaggf dclcpsgpsc sgdcpheggl khngqwilr edrcsvcsck
661  dgkifcrrta cdcqnpnvdl fccpecdtrv tsqcldqsgq klyrsgdnwt hscqqcrcle
721  geadcwplac pslsceytai fegeccprcv sdpcladnia ydirktclds sgisrlsgav
781  wtmagspctt cqckngrvcc svdlvclenn
```

Figure 6

```
   1 gcgttggtgc gccctgcttg gcgggggggcc tccggagcga tgccgatgga tgtgatttta
  61 gttttgtggt tctgtgtgtg caccgccagg acagtgctgg gctttgggat ggaccctgac
 121 cttcagatgg acatcatcac tgaacttgac cttgtgaaca ccaccctggg cgtcactcag
 181 gtggctggac tacacaatgc cagtaaggca tttctgtttc aagatgtaca gagagagatc
 241 cactcagccc ctcatgtgag tgagaagctg atccagctat tccggaataa gagtgagttt
 301 acctttttgg ctacagtgca gcagaagccg tccacctcag gggtgatact gtcgatccgg
 361 gagctggaac acagctattt tgaactggag agcagtggcc aagagaaga gatacgctat
 421 cattacatcc atggcggcaa gcccaggact gaggcccttc cctaccgcat ggccgatgga
 481 cagtggcaca aggtcgcgct gtctgtgagc gcctctcacc tcctactcca tgtcgactgc
 541 aataggattt atgagcgtgt gatagatcct ccggagacca accttcctcc aggaagcaat
 661 aagatcatct tcatgccgaa cggcttcatc acacagtgcc caacctaaa tcgcacttgc
 721 ccaacatgca gtgatttcct gagcctggtt caaggaataa tggatttgca agagcttttg
 781 gccaagatga ctgcaaaact gaattatgca gagacgagac ttggtcaact ggaaaattgc
 841 cactgtgaga agacctgcca agtgagtggg ctgctctaca gggaccaaga ctcctgggta
 901 gatggtgaca actgcaggaa ctgcacatgc aaaagtggtg ctgtggagtg ccgaaggatg
 961 tcctgtcccc cactcaactg ttccccagac tcacttcctg tgcatatttc tggccaatgt
1021 tgtaaagttt gcagaccaaa atgtatctat ggaggaaaag ttcttgctga gggccagcgg
1081 attttaacca agacctgccg ggaatgtcga ggtggagtct tggtaaaaat cacagaagct
1141 tgccctcctt tgaactgctc agagaaggat catattcttc cggagaacca gtgctgcagg
1201 gtctgccgag gtcataactt ctgtgcagaa gcacctaagt gtggagaaaa ctcggaatgc
1261 aaaaattgga atacaaaagc gacttgtgag tgcaagaatg gatacatctc tgtccaggc
1321 aactctgcat actgtgaaga tatcgatgag tgtgcagcaa agatgcacta ctgtcatgcc
1381 aacacggtgt gtgtcaactt gccgggtta tatcgctgtg actgcatccc aggatacatc
1441 cgtgtggatg acttctcttg tacggagcat gatgattgtg gcagcggaca acacaactgt
1501 gacaaaaatg ccatctgtac caacacagtc cagggacaca gctgtacctg ccagccaggc
1561 tacgtgggaa atggtactgt ctgcaaagca ttctgtgaag aggttgcag atacggaggt
1621 acctgtgtgg cccctaacaa atgtgtctgt ccttctggat tcacaggaag ccactgtgag
1681 aaagatattg atgaatgtgc agagggattc gttgagtgcc acaaccactc ccgctgcgtt
1741 aaccttccag ggtggtacca ctgtgagtgc agaagcggtt tccatgacga tgggacctat
1801 tcactgtccg gggagtcctg cattgatatt gatgaatgtg ccttaagaac tcacacttgt
1861 tggaatgact ctgcctgcat caacttagca ggaggatttg actgcctgtg tccctctggg
1921 ccctcctgct ctggtgactg tccccacgaa gggggggctga agcataatgg gcaggtgtgg
1981 attctgagag aagacaggtg ttcagtctgt tcctgtaagg atgggaagat attctgccgg
2041 cggacagctt gtgattgcca gaatccaaat gttgaccttt tctgctgccc agagtgtgac
2101 accagggtca ctagccaatg tttagatcaa agcggacaga agctctatcg aagtggagac
2161 aactggaccc acagctgcca gcagtgccga tgtctggaag gagaggcaga ctgctggcct
2221 ctagcttgcc ctagtttgag ctgtgaatac acagccatct tgaaggaga gtgttgtccc
2281 cgctgtgtca gtgaccctg cctggctgat aatattgcct atgacatcag aaaaacttgc
2341 ctggacagct ctggtatttc gaggctgagc ggcgcagtgt ggacaatggc tggatctccc
2401 tgtacaacct gtcaatgcaa gaatgggaga gtctgctgct ctgtggatct ggtgtgtctt
2461 gagaataact gaagatttta aatggactca tcacatgaga aaatggacaa aatgaccatc
2521 caacctgagg aagaggaggg gctgatttct ttttcttttt aaccacagtc aattaccaaa
2581 gtctccatca gaggaaggcg tttgggttgc ctttaccact tgctcatcc ttgctgacct
2641 agtctagatg cctgcagtac cgtgtatttc ggtcgatggt tgttgagtct ccgtgctgta
2701 aatcacattt cccttgtcag atcatttaca gatacattta aaggattcca tgataaatgt
2761 taaagtacct tttgtttatt ttgtgtacca acataataga gacttggcac ca
```

Figure 7

```
Query   1    MPMDLILVVWFCVCTARTVVGFGMDPDLQMDIVTELDLVNTTLGVAQVSGMHNASKAFLF   60
             MPMD+ILV+WFCVCTARTV+GFGMDPDLQMDI+TELDLVNTTLGV QV+G+HNASKAFLF
Sbjct   1    MPMDVILVLWFCVCTARTVLGFGMDPDLQMDIITELDLVNTTLGVTQVAGLHNASKAFLF   60

Query   61   QDIEREIHAAPHVSEKLIQLFQNKSEFTILATVQQKPSTSGVILSIRELEHSYFELESSG   120
             QD++REIH+APHVSEKLIQLF+NKSEFT LATVQQKPSTSGVILSIRELEHSYFELESSG
Sbjct   61   QDVQREIHSAPHVSEKLIQLFRNKSEFTFLATVQQKPSTSGVILSIRELEHSYFELESSG   120

Query   121  LRDEIRYHYIHNGKPRTEALPYRMADGQWHKVALSVSASHLLLHVDCNRIYERVIDPPDT   180
             R+EIRYHYIH GKPRTEALPYRMADGQWHKVALSVSASHLLLHVDCNRIYERVIDPP+T
Sbjct   121  PREEIRYHYIHGGKPRTEALPYRMADGQWHKVALSVSASHLLLHVDCNRIYERVIDPPET   180

Query   181  NLPPGINLWLGQRNQKHGLFKGIIQDGKIIFMPNGYITQCPNLNHTCPTCSDFLSLVQGI   240
             NLPPG NLWLGQRNQKHG FKGIIQDGKIIFMPNG+ITQCPNLN TCPTCSDFLSLVQGI
Sbjct   181  NLPPGSNLWLGQRNQKHGFFKGIIQDGKIIFMPNGFITQCPNLNRTCPTCSDFLSLVQGI   240

Query   241  MDLQELIAKMTAKLNYAETRLSQLENCHCEKTCQVSGLLYRDQDSWVDGDHCRNCTCKSG   300
             MDLQELLAKMTAKLNYAETRL QLENCHCEKTCQVSGLLYRDQDSWVDGD+CRNCTCKSG
Sbjct   241  MDLQELLAKMTAKLNYAETRLGQLENCHCEKTCQVSGLLYRDQDSWVDGDNCRNCTCKSG   300

Query   301  AVECRRMSCPPLNCSPDSLPVHIAGQCCKVCRPKCIYGGKVLAEGQRILTKSCRECRGGV   360
             AVECRRMSCPPLNCSPDSLPVHI+GQCCKVCRPKCIYGGKVLAEGQRILTK+CRECRGGV
Sbjct   301  AVECRRMSCPPLNCSPDSLPVHISGQCCKVCRPKCIYGGKVLAEGQRILTKTCRECRGGV   360

Query   361  LVKITEMCPPLNCSEKDHILPENQCCRVCRGHNFCAEGPKCGENSECKNWNTKATCECKS   420
             LVKITE CPPLNCSEKDHILPENQCCRVCRGHNFCAE PKCGENSECKNWNTKATCECK+
Sbjct   361  LVKITEACPPLNCSEKDHILPENQCCRVCRGHNFCAEAPKCGENSECKNWNTKATCECKN   420

Query   421  GYISVQGDSAYCEDIDECAAKMHYCHANTVCVNLPGLYRCDCVPGYIRVDDFSCTEHDEC   480
             GYISVQG+SAYCEDIDECAAKMHYCHANTVCVNLPGLYRCDC+PGYIRVDDFSCTEHD+C
Sbjct   421  GYISVQGNSAYCEDIDECAAKMHYCHANTVCVNLPGLYRCDCIPGYIRVDDFSCTEHDDC   480

Query   481  GSGQHNCDENAICTNTVQGHSCTCKPGYVGNGTICRAFCEEGCRYGGTCVAPNKCVCPSG   540
             GSGQHNCD+NAICTNTVQGHSCTC+PGYVGNGT+C+AFCEEGCRYGGTCVAPNKCVCPSG
Sbjct   481  GSGQHNCDKNAICTNTVQGHSCTCQPGYVGNGTVCKAFCEEGCRYGGTCVAPNKCVCPSG   540

Query   541  FTGSHCEKDIDECSEGIIECHNHSRCVNLPGWYHCECRSGFHDDGTYSLSGESCIDIDEC   600
             FTGSHCEKDIDEC+EG +ECHNHSRCVNLPGWYHCECRSGFHDDGTYSLSGESCIDIDEC
Sbjct   541  FTGSHCEKDIDECAEGFVECHNHSRCVNLPGWYHCECRSGFHDDGTYSLSGESCIDIDEC   600

Query   601  ALRTHTCWNDSACINLAGGFDCLCPSGPSCSGDCPHEGGLKHNGQVWTLKEDRCSVCSCK   660
             ALRTHTCWNDSACINLAGGFDCLCPSGPSCSGDCPHEGGLKHNGQVW L+EDRCSVCSCK
Sbjct   601  ALRTHTCWNDSACINLAGGFDCLCPSGPSCSGDCPHEGGLKHNGQVWILREDRCSVCSCK   660

Query   661  DGKIFCRRTACDCQNPSADLFCCPECDTRVTSQCLDQNGHKLYRSGDNWTHSCQQCRCLE   720
             DGKIFCRRTACDCQNP+ DLFCCPECDTRVTSQCLDQ+G KLYRSGDNWTHSCQQCRCLE
Sbjct   661  DGKIFCRRTACDCQNPNVDLFCCPECDTRVTSQCLDQSGQKLYRSGDNWTHSCQQCRCLE   720

Query   721  GEVDCWPLTCPNLSCEYTAILEGECCPRCVSDPCLADNITYDIRKTCLDSYGVSRLSGSV   780
             GE DCWPL CP+LSCEYTAI EGECCPRCVSDPCLADNI YDIRKTCLDS G+SRLSG+V
Sbjct   721  GEADCWPLACPSLSCEYTAIFEGECCPRCVSDPCLADNIAYDIRKTCLDSSGISRLSGAV   780

Query   781  WTMAGSPCTTCKCKNGRVCCSVDFECLQNN   810
             WTMAGSPCTTC+CKNGRVCCSVD  CL+NN
Sbjct   781  WTMAGSPCTTCQCKNGRVCCSVDLVCLENN   810
```

METHODS FOR PROMOTING WOUND HEALING AND MUSCLE REGENERATION WITH THE CELL SIGNALING PROTEIN NELL1

RELATED APPLICATIONS

This application is a divisional of U.S. patent application Ser. No. 12/238,882, filed Sep. 26, 2008, the entire content and disclosure of which are incorporated herein by reference. This application is also related to U.S. application Ser. No. 11/192,813, entitled "Cranial and Vertebral Defects Associated with Loss-of-Function of Nell1." This application is also related to U.S. Provisional Application Ser. Nos. 60/995,854 filed on Sep. 28, 2007 and 61/079,446 filed on Jul. 10, 2008 entitled "Treatment of Cardiovascular Disorders Using the Cell Differentiation Signaling Protein Nell1."

Application Ser. No. 12/238,882 asserts the priority of U.S. Provisional Application Ser. No. 60/976,023 filed on Sep. 28, 2007, the contents of which are incorporated herein by reference.

STATEMENT REGARDING FEDERALLY SPONSORED RESEARCH

The United States Government has rights in this invention pursuant to contract no. DE-AC05-00OR22725 between the United States Department of Energy and UT-Battelle, LLC.

FIELD OF THE INVENTION

This invention relates to the field of wound healing and muscle regeneration. In particular, the invention relates to the discovery that Nell1 protein promotes wound healing and muscle regeneration.

BACKGROUND OF THE INVENTION

Wound healing involves a series of complex biological processes whereby injured tissue is repaired, specialized tissue is regenerated, and new tissue is reorganized. The healing of wounds is generally divided into three phases: the inflammatory phase, the proliferative phase, and maturation and remodeling phase.

In the inflammatory phase, the clotting cascade is initiated in order to stop blood loss. In addition, various factors, such as chemokines, cytokines, and growth factors, are released to attract and activate cells that phagocytize debris, bacteria, and damaged tissue.

The proliferative phase is characterized by angiogenesis and rebuilding of the extracellular matrix architecture which includes collagen deposition, granulation tissue formation, and epithelialization. The formation of new blood vessels, such as capillaries, and the formation of extracellular matrix enable activated satellite cell to proliferate, differentiate, and fuse into new muscle fibers.

Typically, the maturation and remodeling phase of wound healing is said to begin when the levels of collagen production and degradation equalize. During maturation, type III collagen, which is prevalent during proliferation, is gradually degraded and the stronger type I collagen is laid down in its place. The originally disorganized collagen fibers are rearranged, cross-linked, and aligned. In addition, the newly regenerated muscle matures and contracts with the reorganization of the scar tissue.

An impairment in any of these complex phases leads to complications in wound healing. Therefore, it would be beneficial to provide methods for promoting wound healing and/or muscle regeneration.

SUMMARY OF THE INVENTION

These and other objectives have been met by the present invention, which provides, in one aspect, a method for promoting healing of a wound in a mammal in need thereof. The method comprises administering to the mammal an effective amount of Nell1 protein or nucleic acid molecule.

In another aspect, the invention provides a method for treating skeletal muscle atrophy in a mammal in need thereof. The method comprises administering to the mammal an effective amount of Nell1 protein or nucleic acid molecule.

For a better understanding of the present invention, together with other and further advantages, reference is made to the following detailed description, and its scope will be pointed out in the subsequent claims.

BRIEF DESCRIPTION OF THE FIGURES

FIG. 1. Amino acid sequence of human Nell1 protein (SEQ ID No: 1).

FIG. 2. Nucleotide sequence encoding human Nell1 (SEQ ID No: 2).

FIG. 3. Amino acid sequence of rat Nell1 protein (SEQ ID No: 3).

FIG. 4. Nucleotide sequence encoding rat Nell1 (SEQ ID No: 4).

FIG. 5. Amino acid sequence of mouse Nell1 (SEQ ID No: 5).

FIG. 6. Nucleotide sequence encoding mouse Nell1 (SEQ ID No: 6).

FIG. 7. Amino acid sequence alignment of the human Nell1 protein (SEQ ID NO: 1) and the mouse Nell1 protein (SEQ ID NO: 5). The functional domains of the human Nell1 protein are found in the essentially same regions as those identified in the mouse Nell1 protein FIGS. 8A and 8B. Nell1 role in blood vessel and capillary network formation.

DETAILED DESCRIPTION OF THE INVENTION

Figures 8A, 8B:
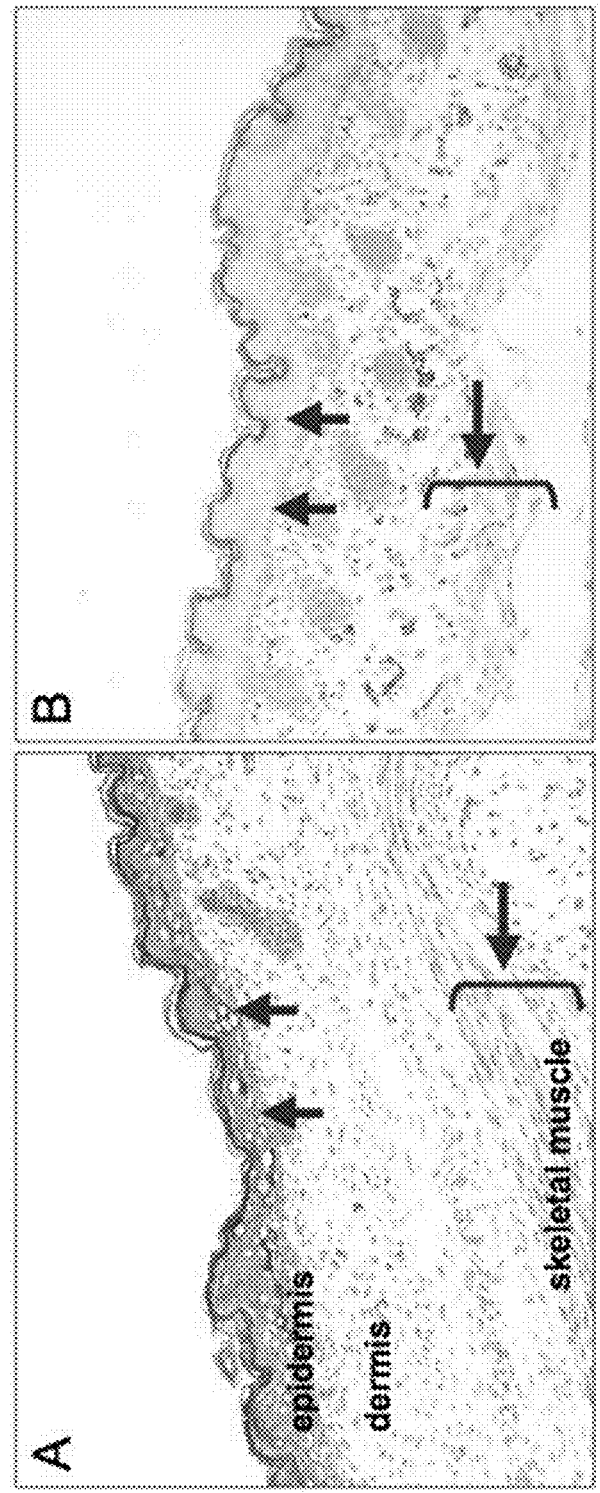

The invention is based on the surprising discovery by the inventor that, Nell1 protein promotes wound healing and muscle regeneration. Throughout this specification, parameters are defined by maximum and minimum amounts. Each minimum amount can be combined with each maximum amount to define a range.

Method for Promoting Healing of a Wound

In one aspect, the present invention provides a method for promoting healing of a wound in a mammal in need thereof. As used herein, the term "promoting healing of a wound" refers to augmenting, improving, increasing, or inducing closure, healing, or repair of a wound. Wound healing is considered to be promoted, for example, if the time of healing a wound treated with Nell1 compared to a wound not treated with Nell1 is decreased by about 10%, preferably decreased by about 25%, more preferably decreased by about 50%, and most preferably decreased by about 75%. Alternatively, wound healing is considered to be promoted if the time and extent of re-acquisition of muscle contractility and function treated with Nell1 compared to a wound not treated with Nell1 is improved by about by about 10%, preferably improved by about 25%, more preferably improved by about 50%, and most preferably improved by about 75%. Conversely, the degree of scar formation can be used to ascertain whether wound healing is promoted.

The wound can be an internal wound or an external wound found in any location of a mammal. A wound is typically caused by physical means, such as mechanical, chemical, bacterial, or thermal means. Wounds can also be caused by accidents, such as a car accident, a fall, injuries sustained in battle (deep lacerations and amputations in soldiers), etc. or by surgical procedures, such as open heart surgery, organ transplants, amputations, and implantations of prosthetics, such as joint and hip replacement, etc. The wound can be an open wound or closed wound.

Open wounds refers to wounds in which the skin is broken. Open wounds include, for example, incisions (i.e., wounds in which the skin is broken by, for instance, a cutting instrument (e.g., knife, razor, etc.)), lacerations (i.e., wounds in which the skin is typically broken by a dull or blunt instrument), abrasions (e.g., generally a superficial wound in which the topmost layers of the skin are scraped off), puncture wounds (typically caused by an object puncturing the skin, such as nail or needle), penetration wounds (e.g., caused by an object such as a knife), and gunshot wounds.

Closed wounds are typically wounds in which the skin is not broken. An example of a closed wound is a contusion.

Any mammal suffering from a wound, such as those described above, is in need of promoting wound healing in accordance with the method of the present invention.

Mammals also in need of promoting wound healing further include any mammal with a disease or condition associated with impaired neovascularization and/or impaired angiogenesis. Neovascularization typically refers to the formation of functional microvascular networks with red blood cell perfusion. Angiogenesis refers generally to the protrusion and outgrowth of capillary buds and sprouts from pre-existing blood vessels. Examples of diseases or conditions associated with impaired neovascularization and/or impaired angiogenesis include diabetes, vascular diseases and aging In one embodiment, the wound healing is promoted in the mammal by promoting regeneration of skeletal muscle. Muscle tissue generally regenerate from reserve myoblasts called satellite cells. The satellite cells are typically found distributed throughout muscle tissue. In undamaged muscle, the majority of satellite cells are quiescent in that they neither differentiate nor undergo cell division.

Following muscle injury or during recovery from disease, satellite cells re-enter the cell cycle, proliferate, and enter existing muscle fibers or undergo differentiation into multinucleate myotubes which form new muscle fiber. The myoblasts eventually yield replacement muscle fibers or fuse into existing muscle fibers, thereby increasing fiber girth.

Thus, the term "regeneration of skeletal muscle" refers to the process by which new skeletal muscle fibers form from muscle progenitor cells. The new skeletal muscle fibers can be new skeletal muscle fibers that replace injured or damaged muscle fibers or new skeletal fibers that fuse into existing muscle fibers.

Skeletal muscle regeneration is considered to be promoted if the number of new fibers is increased at least about 1%, more preferably at least by about 20%, and most preferably by at least about 50%.

In another embodiment, the wound healing is promoted in the mammal by promoting collagen production. Collagen is a fibrous structural protein and a major component of the extracellular matrix. Any type of collagen can be promoted in accordance with the method of the present invention. Examples of types of collagen include, but are not limited to, collagen types I-XXVIII. Preferably, the collagen is type I, collagen type III, collagen type IV, or collagen type VI.

The term "promoting collagen production" refers to an increase in the amount of collagen produced. Any method known to those skilled in the art can use used to determine whether the production of collagen is increased. For example, an increase in collagen production can be determined by analyzing for increased expression of collagen by using, for example, Northern Blot, real time RTPCR, etc. Typically, collagen production is considered to be promoted if the amount of collagen is increased by at least about 1%, more preferably at least by about 10%, and most preferably by at least about 20%.

In one aspect, the method for promoting healing of a wound comprises administering to the mammal in need thereof, an effective amount of a Nell1 protein. The Nell1 protein useful in the methods of the present invention is described below.

In another aspect, the method for promoting healing of a wound comprises administering to the mammal a nucleic acid molecule encoding a Nell1 protein. The nucleic acid molecule useful in the methods of the present invention is described below.

Method for Treating Muscle Atrophy

In another aspect, the present invention provides a method for treating skeletal muscle atrophy in a mammal in need thereof. The term "muscle atrophy" refers to loss of skeletal muscle mass and strength. The atrophy can be found in any location of a mammal.

Skeletal muscle atrophy can be caused by, for example, genetic abnormalities (e.g., mutations or combinations of certain single nucleotide polymorphisms), poor nourishment, poor circulation, loss of hormonal support, disuse of the muscle due to lack of exercise (e.g., bedrest, immobilization of a limb in a cast, etc.), and aging.

Alternatively, skeletal muscle atrophy can be caused by loss of nerve supply to a target organ. Examples of such diseases and conditions include CMT (Charcot Marie Tooth syndrome) poliomyelitis, amyotrophic lateral sclerosis (ALS or Lou Gehrig's disease), and Guillain-Barre syndrome.

Conversely, skeletal muscle atrophy can be a disease of the muscle tissue itself. Examples of such diseases include, but are not limited to, muscular dystrophy, myotonia congenita, and myotonic dystrophy.

Similarly, certain diseases and conditions can also induce skeletal muscle atrophy. Examples of such diseases and conditions include congestive heart failure and liver disease.

Any mammal suffering from skeletal muscle atrophy, such as those described above, can be treated in accordance with the method of the present invention. In one aspect, the method for treating skeletal muscle atrophy includes administering to the mammal an effective amount of a Nell1 protein described below. The Nell1 protein promotes skeletal muscle regeneration, thereby treating the skeletal muscle atrophy.

In another aspect, the method for treating skeletal muscle atrophy comprises administering to the mammal a nucleic acid molecule encoding a Nell1 protein. The nucleic acid molecule useful in the methods of the present invention is described below.

Nell1 Protein

Nell1 protein is a protein kinase C (PKC) β-binding protein. The Nell1 protein useful in the methods of the present invention can comprise a polypeptide having the same amino acid sequence as Nell1 protein derived from nature, a recombinant Nell1 protein, a homolog thereof, or fragments thereof. Accordingly, a "Nell1 protein" as used herein, also refers to homologs and fragments thereof.

The amino acid sequence of Nell1 protein is highly conserved across species. For example, the mouse Nell1 protein shares about 93% sequence identity with the human Nell1 protein, which, in turn, shares about 90% sequence identity with the rat Nell1 protein. FIG. 7 shows a sequence alignment between human Nell1 protein and mouse Nell1 protein.

Since the amino acid sequence of Nell1 protein is highly conserved, the naturally occurring amino acid sequence of Nell1 protein can be from any animal. For example, the Nell1 protein can be human Nell1, rat Nell1, or mouse Nell1.

The amino acid sequence of human Nell1 protein can be found at GenBank Accession No. AAH96102, and is shown in FIG. 1 (SEQ. ID. NO: 1). Due to the degeneracy of the genetic code, an example of a nucleotide sequence which encodes SEQ. ID. NO: 1 is shown in FIG. 2 (SEQ. ID. NO:2).

The amino acid sequence of rat Nell1 protein can be found at GenBank Accession No. NP_112331, and is shown in FIG. 3 (SEQ. ID. NO: 3). An example of a nucleotide sequence which encodes SEQ. ID. NO: 3 is shown in FIG. 4 (SEQ. ID. NO: 4).

The amino acid sequence of mouse Nell1 protein can be found at GenBank Accession No. NP_001032995, and is shown in FIG. 5 (SEQ. ID. NO: 5). An example of a nucleotide sequence which encodes SEQ. ID. NO: 5 is shown in FIG. 6 (SEQ. ID. NO: 6).

The structure of Nell1 proteins has been characterized (see, e.g., Kuroda et al., 1999a; Kuroda et al., 1999b, Desai et al., 2006). For example, the mouse Nell1 protein (SEQ ID NO: 5) is a protein of 810 amino acids, having a secretion signal peptide (amino acids 1 to 16), an N-terminal TSP-like module (amino acids #29 to 213), a Laminin G region (amino acids #86 to 210), von Willebrand factor C domains (amino acids #273 to 331 and 699 to 749), and a $Ca^{2+}$-binding EGF-like domains (amino acids #549 to 586).

The secretion signal peptide domain of Nell1 protein is an amino acid sequence in the protein that is generally involved in transport of the protein to cell organelles where it is processed for secretion outside the cell. The N-terminal TSP-like module is generally associated with heparin binding. von Willebrand factor C domains are generally involved with oligomerization of Nell1. Laminin G domains of Nell1 protein are generally involved in adherence of Nell1 protein to specific cell types or other extracellular matrix proteins. The interaction of such domains with their counterparts is generally associated with, for example, processes such as differentiation, adhesion, cell signaling or mediating specific cell-cell interactions in order to promote cell proliferation and differentiation. The $Ca^{2+}$-binding EGF-like domains of Nell1 binds protein kinase C beta, which is typically involved in cell signaling pathways in growth and differentiation Homologs of Nell1 protein include, for example, a substitution mutant, a mutant having an addition or insertion, or a deletion mutant of the protein. Substitutions in a sequence of amino acids are preferably with equivalent amino acids. Groups of amino acids known to be of equivalent character are listed below:
 (a) Ala(A), Ser(S), Thr(T), Pro(P), Gly(G);
 (b) Asn(N), Asp(D), Glu(E), Gln(O);
 (c) His(H), Arg(R), Lys(K);
 (d) Met(M), Leu(L), Ile(I), Val(V); and
 (e) Phe(F), Tyr(Y), Trp(W).

Any substitutions, additions, and/or deletions in an amino acid sequence are permitted provided that the Nell1 protein is functional. An amino acid sequence that is substantially identical to another sequence, but that differs from the other sequence by means of one or more substitutions, additions, and/or deletions, is considered to be an equivalent sequence.

In order to compare a first amino acid to a second amino acid sequence for the purpose of determining homology, the sequences are aligned so as to maximize the number of identical amino acid residues. The sequences of highly homologous proteins can usually be aligned by visual inspection. If visual inspection is insufficient, the amino acid molecules may be aligned in accordance with methods known in the art. Examples of suitable methods include those described by George, D. G. et al., in Macromolecular Sequencing and Synthesis, Selected Methods and Applications, pages 127-149, Alan R. Liss, Inc. (1988), such as formula 4 at page 137 using a match score of 1, a mismatch score of 0, and a gap penalty of −1.

Preferably, less than 15%, more preferably less than 10%, and still more preferably less than 5% of the number of amino acid residues in the sequence of Nell1 are different (i.e., substituted for, inserted into, or deleted from). More preferably still, less than 3%, yet more preferably less than 2% and optimally less than 1% of the number of amino acid residues in a sequence are different from those in a naturally occurring sequence.

Preferably, the substitutions, additions, and/or deletions are not made in the conserved regions of the protein or in the functional domain of the protein. Examples of conserved regions of Nell1 protein include the secretory signal, Willebrand like domain, thrombospondin-like domains and laminin-like domains. Examples of functional domains of Nell1 protein include the EGF like domains. Thus, substitutions, additions, and/or deletions in the non-conserved and/or non-functional regions of the protein can typically be made without affecting the function of Nell1 protein.

A Nell1 protein further includes Nell1 protein fragments that retain the ability to promote healing of wounds and skeletal muscle regeneration. Preferably, the Nell1 protein fragment contains one or more of the conserved regions and/or functional domains of the protein. For example, the Nell1 protein fragments can comprise the EGF like domains and/or the von Willebrand like domain of Nell1 protein.

The minimum length of a Nell1 functional fragment is typically at least about 10 amino acids residues in length, more typically at least about 20 amino acid residues in length, even more typically at least about 30 amino acid residues in length, and still more typically at least about 40 amino acid residues in length. As stated above, wild type Nell1 protein is approximately about 810 amino acid residues in length. A Nell1 functional derivative can be at most about 810 amino acid residues in length. For example, a Nell1 functional derivative can be at most at most about 820, 805, 800, 790, 780, 750, 600, 650 600, 550, etc. amino acid residues in length Once a Nell1 functional protein homolog or Nell1 functional protein fragment is made, such protein can be tested to determine whether it retains substantially the activity or function of a wild type Nell1 protein. For example, the ability of a Nell1 homolog or fragment to bind PKC beta can be tested. Suitable assays for assessing the binding of Nell1 to PKC beta is described in e.g., Kuroda et al. (*Biochemical Biophysical Research Comm.* 265: 752-757 (1999b)). For example, protein-protein interaction can be analyzed by using the yeast two-hybrid system. Briefly, a modified Nell1 protein can be fused with GAL4 activating domain and the regulatory domain of PKC can be fused with the GAL4 DNA-binding domain.

In addition, the ability of a Nell1 protein homolog or fragment to stimulate differentiation of precursor cells, such as skeletal satellite cells, to maturity can be tested. Maturity of skeletal muscle cells can be assessed cellularly (histology)

and molecularly (expression of skeletal muscle-specific proteins or extracellular matrix materials). Still further, a Nell1 protein homolog or fragment can be tested for its ability to drive osteoblast precursors to mature bone cells, by detecting expression of late molecular bone markers or mineralization (i.e., calcium deposits). By comparing the activity of a Nell1 protein homolog or fragment with that of a wild type Nell1 protein in one or more of the assays such as those described above, one can determine whether such homologs or fragments retain substantially the activity or function of a wild type Nell1 protein.

The Nell1 protein, functional homolog or functional fragment may be prepared by methods that are well known in the art. One such method includes isolating or synthesizing DNA encoding the Nell1 protein, and producing the recombinant protein by expressing the DNA, optionally in a recombinant vector, in a suitable host cell. Suitable methods for synthesizing DNA are described by Caruthers et al. 1985. Science 230:281-285 and DNA Structure, Part A: Synthesis and Physical Analysis of DNA, Lilley, D. M. J. and Dahlberg, J. E. (Eds.), Methods Enzymol., 211, Academic Press, Inc., New York (1992). Examples of suitable Nell1 nucleic acid sequences include SEQ. ID. NOs: 2, 4, and 6.

The Nell1 protein may also be made synthetically, i.e. from individual amino acids, or semisynthetically, i.e. from oligopeptide units or a combination of oligopeptide units and individual amino acids. Suitable methods for synthesizing proteins are described by Stuart and Young in "Solid Phase Peptide Synthesis," Second Edition, Pierce Chemical Company (1984), Solid Phase Peptide Synthesis, Methods Enzymol., 289, Academic Press, Inc, New York (1997). Examples of suitable Nell1 amino acid sequences include SEQ. ID. NOs: 1, 3, 5, homologs thereof, and fragments thereof.

Nell1 Nucleic Acid Molecules

Any nucleic acid sequence that encodes for Nell1 protein can be used in the methods of the present invention. Suitable nucleic acid molecules encoding Nell1 protein for use in the methods of the present invention include nucleic acid molecules having a nucleotide sequence as set forth in SEQ. ID. NOs: 2, 4 and 6, as well as degenerate sequences thereof. As used herein, the term "degenerate sequence" refers to a sequence formed by replacing one or more codons in the nucleotide sequence encoding wild type Nell1 protein with degenerate codes which encode the same amino acid residue (e.g., GAU and GAC triplets each encode the amino acid Asp). The nucleic acid molecules can be incorporated into recombinant vectors suitable for use in gene therapy.

Examples of vectors suitable for use in gene therapy may be any vector that comprises a nucleic acid sequence capable of expressing the Nell1 protein in a mammal, especially a human, in need of such therapy. The suitable vector may be for example a viral vector (e.g., such as an adenovirus vector, adeno-associated virus (AAV) vector, retroviral vector, herpes simplex viral vector, polio virues and vaccinia vectors), nonviral vectors (e.g., plasmid vectors), etc. See for example: Ledley 1996. Pharmaceutical Research 13:1595-1614 and Verma et al. Nature 1997. 387:239-242.

Examples of retroviral vectors include, but are not limited to, Moloney murine leukemia virus (MoMuLV), Harvey murine sarcoma virus (HaMuSV), murine mammary tumor virus (MuMTV), and Rous Sarcoma Virus (RSV)-derived recombinant vectors. A Nell1-coding nucleotide sequence can be placed in an operable linkage to a promoter in the expression vector, wherein the promoter directs the expression of the Nell1 protein in the targeted tissue or cells, and includes both a constitutive promoter and a tissue or cell-specific promoter Administration The Nell1 protein or nucleic acid molecule is administered to a mammal in need thereof. The mammal may be a farm animal, such as a goat, horse, pig, or cow; a pet animal, such as a dog or cat; a laboratory animal, such as a mouse, rat, or guinea pig; or a primate, such as a monkey, orangutan, ape, chimpanzee, or human. In a preferred embodiment, the mammal is a human.

The Nell1 protein or nucleic acid molecule can be incorporated in a pharmaceutical composition suitable for use as a medicament, for human or animal use. The pharmaceutical compositions may be for instance, in an injectable formulation, a liquid, cream or lotion for topical application, an aerosol, a powder, granules, tablets, suppositories or capsules, such as for instance, enteric coated capsules etc. The pharmaceutical compositions may also be delivered in or on a lipid formulation, such as for instance an emulsion or a liposome preparation. The pharmaceutical compositions are preferably sterile, non-pyrogenic and isotonic preparations, optionally with one or more of the pharmaceutically acceptable additives listed below.

Pharmaceutical compositions of Nell1 protein or nucleic acid molecule are preferably stable compositions which may comprise one or more of the following: a stabilizer, a surfactant, preferably a nonionic surfactant, and optionally a salt and/or a buffering agent. The pharmaceutical composition may be in the form of an aqueous solution, or in a lyophilized form.

The stabilizer may, for example, be an amino acid, such as for instance, glycine; or an oligosaccharide, such as for example, sucrose, tetralose, lactose or a dextram. Alternatively, the stabilizer may be a sugar alcohol, such as for instance, mannitol; or a combination thereof. Preferably the stabilizer or combination of stabilizers constitutes from about 0.1% to about 10% weight for weight of the Nell1 protein.

The surfactant is preferably a nonionic surfactant, such as a polysorbate. Some examples of suitable surfactants include Tween20, Tween80; a polyethylene glycol or a polyoxyethylene polyoxypropylene glycol, such as Pluronic F-68 at from about 0.001% (w/v) to about 10% (w/v).

The salt or buffering agent may be any salt or buffering agent, such as for example, sodium chloride, or sodium/potassium phosphate, respectively. Preferably, the buffering agent maintains the pH of the pharmaceutical composition in the range of about 5.5 to about 7.5. The salt and/or buffering agent is also useful to maintain the osmolality at a level suitable for administration to a human or an animal. Preferably the salt or buffering agent is present at a roughly isotonic concentration of about 150 mM to about 300 mM.

The pharmaceutical composition comprising Nell1 protein or nucleic acid molecule may additionally contain one or more conventional additive. Some examples of such additives include a solubilizer such as for example, glycerol; an antioxidant such as for example, benzalkonium chloride (a mixture of quaternary ammonium compounds, known as "quats"), benzyl alcohol, chloretone or chlorobutanol; anaesthetic agent such as for example a morphine derivative; or an isotonic agent etc., such as described above. As a further precaution against oxidation or other spoilage, the pharmaceutical compositions may be stored under nitrogen gas in vials sealed with impermeable stoppers.

An effective amount of the Nell1 protein or nucleic acid molecule, preferably in a pharmaceutical composition, may be administered to a human or an animal in need thereof by any of a number of well-known methods. For example, the Nell1 protein or nucleic acid molecule may be administered systemically or locally, for example by injection.

The systemic administration of the Nell1 protein or nucleic acid molecule may be by intravenous, subcutaneous, intraperitoneal, intramuscular, intrathecal or oral administration. Alternatively, the Nel-1 protein or nucleic acid molecule may be applied topically in appropriate situations. Such situations include, for example, skin abrasions and surface wounds.

The Nell1 protein can be administered by a cell based gene therapy. For example, allogeneic or xenogenic donor cells are genetically modified in vitro to express and secrete Nell1 protein. The genetically modified donor cells are then subsequently implanted into the mammal in need for delivery of Nell1 protein in vivo. Examples of suitable cells include, but are not limited to, endothelial cells, epithelial cells, fibroblasts, myoblasts, satellite cells, and skeletal muscle cells, stem cells, such as adult stem cells, embryonic stem cells, and cord blood stem cells.

Alternatively, the genetically modified donor cells can be incorporated into a matrix containing an appropriate microenvironment to maintain, for a given time, the viability and growth of the genetically modified donor cells. The matrix can be applied to, for example, a surface wound. Expression and secretion of Nell1 by the genetically modified donor cells promotes healing of the wound. After the wound is healed, the matrix can be removed. Examples of suitable matrices include, but are not limited to, wound dressings, collagen matrix, patches, and hydrogels.

An effective amount of a pharmaceutical composition of the invention is any amount that is effective to achieve its purpose. The effective amount, usually expressed in mg/kg can be determined by routine methods during pre-clinical and clinical trials by those of skill in the art.

EXAMPLES

Example 1

Expression of the Nell1 Protein in the Skin and Underlying Muscle Cells

Sagittal sections of whole fetal bodies collected a day before birth were analyzed by immunohistochemical methods using an antibody for the Nell1 protein. The red/pink staining in the epidermis, dermis and underlying skeletal muscle of normal fetal mice (FIG. 8A) indicates the abundant presence of the Nell1 protein. Note the absence of the protein in the Nell1$^{6R}$ mutant (FIG. 8B) and the resulting disordered architecture of dermis and underlying muscle.

Example 2

Genes in the Nell1 Pathway

Genes that are part of the Nell1 pathway during musculoskeletal development were determined by quantitative real time PCR (qRTPCR) assays and microarray analyses of fetal bodies (15 and 18 days of gestation). The role of Nell1 in muscle formation was revealed by the immunohistochemistry and microarray data. The genes in the Nell1 pathway associated with wound healing and muscle regeneration include Tenascin b (Tnxb), Tenascin C (Tnc), osteoblast specific factor (Osf2), periostin, Matrilin 2 (Matn2), Collagen VI a 1 (Col6a1), protein kinase C (PKC), Notch 3, TAL/SCL, Bcap31, Collagen IV a 1 (Col4a1).

Example 3

Nell1 Promotes Wound Healing and Muscle Regeneration in a Poor Wound Healing Mouse Strain Severe muscle injury is induced in adult SJL/J mice a strain, known to be a genetically poor wound healer. The ability of purified recombinant human Nell1 protein is tested in the wound healing of severely lacerated leg muscles of SJL/J mice. Wounding is induced by surgically removing a sliver of muscle (approximately 5 mm long×1 mm wide×2 mm deep) from the left gastrocnemius muscle of adult mice (4-5 months old) and the skin wound is sutured. On the third day after wounding, 5 mice are given phosphate buffered saline (PBS) solution to serve as controls, 5 mice are treated with 312 ng Nell1 protein (Dose I) and another 5 mice with 624 ng protein (Dose II). Nell1 Protein diluted in PBS (8 microliters) is administered directly along the entire length of the gaping muscle wound by dripping from a microinjector with a fine gauge needle. Wound healing is assessed one week post-treatment. Observations are made under a dissecting microscope.

Example 4

Nell1 Promotes Muscle Regeneration in Chemically-Induced Type I Diabetic Mice

Type I diabetes is induced in mice by streptozotocin (STZ), an alkylating agent that destroys the pancreatic islet cells. Commercially produced diabetic mice are purchased from The Jackson Laboratory. Diabetic mice are generated by the following method: At 8 weeks of age, one daily intraperitoneal injection of STZ for five consecutive days. Two weeks after the last STZ injection, mice are weighed and blood glucose levels are measured. Mice with at least 300-400 mg/dL blood glucose levels are considered diabetic. Wounding surgeries are performed as previously described in Example 3, but are done on younger adult mice (three months old) due to the severity of the induced diabetes (diabetic mice are already at 400-600 mg/dL at this stage). Four diabetic mice are given PBS as controls and four are given 312 ng of purified recombinant human Nell1 protein diluted in PBS. Protein is given two days after wounding and treatment effects are examined after one week.

Example 5

Nell1 Promotes Muscle Regeneration in Aged Mice

Ten to twelve month old C57BL/6 mice are lacerated in the leg muscle as described Examples 3 and 4. Nell1 protein is injected or administered as described in Examples 3 and 4 directly into the wound site. The mice are euthanized at different time points, wounds are evaluated and their tissue is collected for histological analysis.

Example 6

Nell1 Promotes Wound Healing of Chemically and Heat Damaged Muscle Tissue

Mammals with chemically or heat-induced muscle damage are treated with Nell1 protein in the wound and areas immediately bordering the damaged tissue. This can be a single administration of the appropriate Nell1 protein level or can be incorporated into wound dressings, bandages or ointments to provide a lower dose but continuous/time release introduction of Nell1. In addition, tissue grafts can be implanted into the damaged area along with the Nell1 protein introduced in the boundaries of the graft in order to promote vascularization and success of the tissue grafts onto the damaged areas.

Thus, while there have been described what are presently believed to be the preferred embodiments of the invention, changes and modifications can be made to the invention and other embodiments will be know to those skilled in the art, which fall within the spirit of the invention, and it is intended to include all such other changes and modifications and embodiments as come within the scope of the claims as set forth herein below

What is claimed is:

1. A method for promoting healing of a skeletal muscle wound in a mammal, the method comprising:
   (a) locally administering to the skeletal muscle wound an effective amount of an autologous or allogeneic cell comprising an expression vector encoding a Nell1 protein,
   wherein the cell of step (a) expresses the Nell1 protein and is selected from the group consisting of an endothelial cell, epithelial cell, fibroblast, myoblast, satellite cell, skeletal muscle cell, and adult stem cell, and wherein said Nell1 protein has an amino acid sequence having at least 90% sequence identity to SEQ ID NO: 1, 3, or 5 and stimulates differentiation of precursor cells to maturity, thereby promoting healing of the skeletal muscle wound.

2. The method according to claim 1, wherein the Nell1 protein comprises SEQ ID NO: 1.

3. The method according to claim 1, wherein the Nell1 protein comprises SEQ ID NO: 3.

4. The method according to claim 1, wherein the Nell1 protein comprises SEQ ID NO: 5.

5. The method according to claim 1, wherein the Nell1 protein is a human Nell1 protein.

6. The method according to claim 1, wherein the mammal is a human.

7. The method according to claim 1, wherein local administration is by injection.

8. The method according to claim 1, wherein local administration is topical.

9. The method according to claim 1, wherein the mammal suffers from a disease or condition associated with impaired neovascularization or impaired angiogenesis.

10. The method according to claim 9, wherein the mammal has diabetes, a vascular disease, or is aging.

11. The method according to claim 1, wherein the skeletal muscle wound is caused by a mechanical, chemical, bacterial, or thermal means.

12. The method according to claim 11, wherein the skeletal muscle wound is caused by thermal means.

13. The method according to claim 1, wherein the cell is incorporated into a matrix.

14. A method for promoting healing of a skin wound in a mammal, the method comprising:
   (a) locally administering to the skin wound an effective amount of an autologous or allogeneic cell comprising an expression vector encoding a Nell1 protein,
   wherein the cell of step (a) expresses the Nell1 protein and is selected from the group consisting of an endothelial cell, epithelial cell, fibroblast, myoblast, satellite cell, skeletal muscle cell, and adult stem cell, and wherein said Nell1 protein has an amino acid sequence having at least 90% sequence identity to SEQ ID NO: 1, 3, or 5 and stimulates differentiation of precursor cells to maturity, thereby promoting healing of the skin wound.

15. The method according to claim 14, wherein the skin wound is caused by mechanical, chemical, bacterial, or thermal means.

16. The method according to claim 15, wherein the skin wound is caused by thermal means.

17. The method according to claim 14, wherein the Nell1 protein comprises SEQ ID NO: 1.

18. The method according to claim 14, wherein the Nell1 protein comprises SEQ ID NO: 3.

19. The method according to claim 14, wherein the Nell1 protein comprises SEQ ID NO: 5.

20. The method according to claim 14, wherein the Nell1 protein is a human Nell1 protein.

21. The method according to claim 14, wherein the mammal is a human.

22. The method according to claim 14, wherein said skin wound is an open wound.

23. The method according to claim 22, wherein said open wound is selected from the group consisting of an incision, a laceration, an abrasion, a puncture wound, a penetration wound, and a gunshot wound.

24. The method according to claim 14, wherein local administration is by injection.

25. The method according to claim 14, wherein local administration is topical.

26. The method according to claim 14, wherein the mammal suffers from a disease or condition associated with impaired neovascularization or impaired angiogenesis.

27. The method according to claim 26, wherein the mammal has diabetes, a vascular disease, or is aging.

28. The method according to claim 14, wherein promoting healing of the open wound comprises closure of the wound.

29. The method according to claim 14, wherein the cell is incorporated into a matrix.

30. A method for treating skeletal muscle atrophy in a mammal, the method comprising:
   (a) locally administering to a site of skeletal muscle atrophy an effective amount of an autologous or allogeneic cell comprising an expression vector encoding a Nell1 protein,
   wherein the cell of step (a) expresses the Nell1 protein and is selected from the group consisting of an endothelial cell, epithelial cell, fibroblast, myoblast, satellite cell, skeletal muscle cell, and adult stem cell, and wherein said Nell1 protein has an amino acid sequence having at least 90% sequence identity to SEQ ID NO: 1, 3, or 5 and stimulates differentiation of precursor cells to maturity, thereby treating skeletal muscle atrophy.

31. The method according to claim 30, wherein the Nell1 protein comprises SEQ ID NO: 1.

32. The method according to claim 30, wherein the Nell1 protein comprises SEQ ID NO: 3.

33. The method according to claim 30, wherein the Nell1 protein comprises SEQ ID NO: 5.

34. The method according to claim 30, wherein the Nell1 protein is a human Nell1 protein.

35. The method according to claim 30, wherein the mammal is a human.

36. The method according to claim 30, wherein local administration is by injection.

37. The method according to claim 30, wherein local administration is topical.

38. The method according to claim 30, wherein the cell is incorporated into a matrix.

39. A method for promoting healing of a wound caused by thermal means in a mammal, the method comprising:
(a) locally administering to the wound an effective amount of an autologous or allogeneic cell comprising an expression vector encoding a Nell1 protein,
wherein the cell of step (a) expresses the Nell1 protein and is selected from the group consisting of an endothelial cell, epithelial cell, fibroblast, myoblast, satellite cell, skeletal muscle cell, and adult stem cell, and wherein said Nell1 protein has an amino acid sequence having at least 90% sequence identity to SEQ ID NO: 1, 3, or 5 and stimulates differentiation of precursor cells to maturity, thereby promoting healing of the wound caused by thermal means.

40. The method according to claim 39, wherein the Nell1 protein comprises SEQ ID NO: 1.

41. The method according to claim 39, wherein the Nell1 protein comprises SEQ ID NO: 3.

42. The method according to claim 39, wherein the Nell1 protein comprises SEQ ID NO: 5.

43. The method according to claim 39, wherein the Nell1 protein is a human Nell1 protein.

44. The method according to claim 39, wherein the mammal is a human.

45. The method according to claim 39, wherein local administration is by injection.

46. The method according to claim 39, wherein local administration is topical.

47. The method according to claim 39, wherein the mammal suffers from a disease or condition associated with impaired neovascularization or impaired angiogenesis.

48. The method according to claim 47, wherein the mammal has diabetes, a vascular disease, or is aging.

49. The method according to claim 39, wherein promoting healing of the wound comprises closure of the wound.

50. The method according to claim 39, wherein the cell is incorporated into a matrix.

51. The method according to claim 1, wherein said method comprises locally administering to the skeletal muscle wound an effective amount of an allogeneic cell expressing a Nell1 protein.

52. The method according to claim 14, wherein said method comprises locally administering to the wound an effective amount of an allogeneic cell expressing a Nell1 protein.

53. The method according to claim 30, wherein said method comprises locally administering to the site of skeletal muscle atrophy an effective amount of an allogeneic cell expressing a Nell1 protein.

54. The method according to claim 39, wherein said method comprises locally administering to the wound an effective amount of an allogeneic cell expressing a Nell1 protein.

55. The method according to claim 13, wherein said matrix comprises a wound dressing.

56. The method according to claim 29, wherein said matrix comprises a wound dressing.

57. The method according to claim 38, wherein said matrix comprises a wound dressing.

58. The method according to claim 50, wherein said matrix comprises a wound dressing.

59. The method according to claim 1, wherein the mammal is a horse.

60. The method according to claim 14, wherein the mammal is a horse.

61. The method according to claim 30, wherein the mammal is a horse.

62. The method according to claim 39, wherein the mammal is a horse.

63. The method according to claim 1, wherein said autologous or allogeneic cell comprises a nucleotide sequence having at least 90% sequence identity to SEQ ID NO: 2, 4, or 6.

64. The method according to claim 63, wherein said nucleotide sequence comprises SEQ ID NO: 2, 4, or 6.

65. The method according to claim 63, wherein said nucleotide sequence is operably linked to a promoter in an expression vector.

66. The method according to claim 14, wherein said autologous or allogeneic cell comprises a nucleotide sequence having at least 90% sequence identity to SEQ ID NO: 2, 4, or 6.

67. The method according to claim 66, wherein said nucleotide sequence comprises SEQ ID NO: 2, 4, or 6.

68. The method according to claim 66, wherein said nucleotide sequence is operably linked to a promoter in an expression vector.

69. The method according to claim 30, wherein said autologous or allogeneic cell comprises a nucleotide sequence having at least 90% sequence identity to SEQ ID NO: 2, 4, or 6.

70. The method according to claim 69, wherein said nucleotide sequence comprises SEQ ID NO: 2, 4, or 6.

71. The method according to claim 69, wherein said nucleotide sequence is operably linked to a promoter in an expression vector.

72. The method according to claim 39, wherein said autologous or allogeneic cell comprises a nucleotide sequence having at least 90% sequence identity to SEQ ID NO: 2, 4, or 6.

73. The method according to claim 72, wherein said nucleotide sequence comprises SEQ ID NO: 2, 4, or 6.

74. The method according to claim 72, wherein said nucleotide sequence is operably linked to a promoter in an expression vector.

75. The method according to claim 1, wherein said effective amount of said autologous or allogeneic cell is administered to said wound about 2 to about 3 days after wounding.

76. The method according to claim 14, wherein said effective amount of said autologous or allogeneic cell is administered to said wound about 2 to about 3 days after wounding.

77. The method according to claim 39, wherein said effective amount of said autologous or allogeneic cell is administered to said wound about 2 to about 3 days after wounding.

* * * * *

SEQUENCE LISTING

```
<160> NUMBER OF SEQ ID NOS: 6

<210> SEQ ID NO 1
<211> LENGTH: 810
<212> TYPE: PRT
<213> ORGANISM: Homo sapiens

<400> SEQUENCE: 1

Met Pro Met Asp Leu Ile Leu Val Val Trp Phe Cys Val Cys Thr Ala
1               5                   10                  15

Arg Thr Val Val Gly Phe Gly Met Asp Pro Asp Leu Gln Met Asp Ile
                20                  25                  30

Val Thr Glu Leu Asp Leu Val Asn Thr Thr Leu Gly Val Ala Gln Val
            35                  40                  45

Ser Gly Met His Asn Ala Ser Lys Ala Phe Leu Phe Gln Asp Ile Glu
        50                  55                  60

Arg Glu Ile His Ala Ala Pro His Val Ser Glu Lys Leu Ile Gln Leu
65                  70                  75                  80

Phe Arg Asn Lys Ser Glu Phe Thr Ile Leu Ala Thr Val Gln Gln Lys
                85                  90                  95

Pro Ser Thr Ser Gly Val Ile Leu Ser Ile Arg Glu Leu Glu His Ser
                100                 105                 110

Tyr Phe Glu Leu Glu Ser Ser Gly Leu Arg Asp Glu Ile Arg Tyr His
            115                 120                 125

Tyr Ile His Asn Gly Lys Pro Arg Thr Glu Ala Leu Pro Tyr Arg Met
        130                 135                 140

Ala Asp Gly Gln Trp His Lys Val Ala Leu Ser Val Ser Ala Ser His
145                 150                 155                 160

Leu Leu Leu His Val Asp Cys Asn Arg Ile Tyr Glu Arg Val Ile Asp
                165                 170                 175

Pro Pro Asp Thr Asn Leu Pro Pro Gly Ile Asn Leu Trp Leu Gly Gln
                180                 185                 190

Arg Asn Gln Lys His Gly Leu Phe Lys Gly Ile Ile Gln Asp Gly Lys
            195                 200                 205

Ile Ile Phe Met Pro Asn Gly Tyr Ile Thr Gln Cys Pro Asn Leu Asn
        210                 215                 220

His Thr Cys Pro Thr Cys Ser Asp Phe Leu Ser Leu Val Gln Gly Ile
225                 230                 235                 240

Met Asp Leu Gln Glu Leu Leu Ala Lys Met Thr Ala Lys Leu Asn Tyr
                245                 250                 255

Ala Glu Thr Arg Leu Ser Gln Leu Glu Asn Cys His Cys Glu Lys Thr
                260                 265                 270

Cys Gln Val Ser Gly Leu Leu Tyr Arg Asp Gln Asp Ser Trp Val Asp
            275                 280                 285

Gly Asp His Cys Arg Asn Cys Thr Cys Lys Ser Gly Ala Val Glu Cys
        290                 295                 300

Arg Arg Met Ser Cys Pro Pro Leu Asn Cys Ser Pro Asp Ser Leu Pro
305                 310                 315                 320
```

-continued

```
Val His Ile Ala Gly Gln Cys Cys Lys Val Cys Arg Pro Lys Cys Ile
                325                 330                 335
Tyr Gly Gly Lys Val Leu Ala Glu Gly Gln Arg Ile Leu Thr Lys Ser
            340                 345                 350
Cys Arg Glu Cys Arg Gly Gly Val Leu Val Lys Ile Thr Glu Met Cys
        355                 360                 365
Pro Pro Leu Asn Cys Ser Glu Lys Asp His Ile Leu Pro Glu Asn Gln
    370                 375                 380
Cys Cys Arg Val Cys Arg Gly His Asn Phe Ala Glu Gly Pro Lys
385                 390                 395                 400
Cys Gly Glu Asn Ser Glu Cys Lys Asn Trp Asn Thr Lys Ala Thr Cys
                405                 410                 415
Glu Cys Lys Ser Gly Tyr Ile Ser Val Gln Gly Asp Ser Ala Tyr Cys
            420                 425                 430
Glu Asp Ile Asp Glu Cys Ala Ala Lys Met His Tyr Cys His Ala Asn
        435                 440                 445
Thr Val Cys Val Asn Leu Pro Gly Leu Tyr Arg Cys Asp Cys Val Pro
    450                 455                 460
Gly Tyr Ile Arg Val Asp Asp Phe Ser Cys Thr Glu His Asp Glu Cys
465                 470                 475                 480
Gly Ser Gly Gln His Asn Cys Asp Glu Asn Ala Ile Cys Thr Asn Thr
                485                 490                 495
Val Gln Gly His Ser Cys Thr Cys Lys Pro Gly Tyr Val Gly Asn Gly
            500                 505                 510
Thr Ile Cys Arg Ala Phe Cys Glu Glu Gly Cys Arg Tyr Gly Gly Thr
        515                 520                 525
Cys Val Ala Pro Asn Lys Cys Val Cys Pro Ser Gly Phe Thr Gly Ser
    530                 535                 540
His Cys Glu Lys Asp Ile Asp Glu Cys Ser Glu Gly Ile Ile Glu Cys
545                 550                 555                 560
His Asn His Ser Arg Cys Val Asn Leu Pro Gly Trp Tyr His Cys Glu
                565                 570                 575
Cys Arg Ser Gly Phe His Asp Asp Gly Thr Tyr Ser Leu Ser Gly Glu
            580                 585                 590
Ser Cys Ile Asp Ile Asp Glu Cys Ala Leu Arg Thr His Thr Cys Trp
        595                 600                 605
Asn Asp Ser Ala Cys Ile Asn Leu Ala Gly Gly Phe Asp Cys Leu Cys
    610                 615                 620
Pro Ser Gly Pro Ser Cys Ser Gly Asp Cys Pro His Glu Gly Gly Leu
625                 630                 635                 640
Lys His Asn Gly Gln Val Trp Thr Leu Lys Glu Asp Arg Cys Ser Val
                645                 650                 655
Cys Ser Cys Lys Asp Gly Lys Ile Phe Cys Arg Arg Thr Ala Cys Asp
            660                 665                 670
Cys Gln Asn Pro Ser Ala Asp Leu Phe Cys Cys Pro Glu Cys Asp Thr
        675                 680                 685
Arg Val Thr Ser Gln Cys Leu Asp Gln Asn Gly His Lys Leu Tyr Arg
    690                 695                 700
Ser Gly Asp Asn Trp Thr His Ser Cys Gln Gln Cys Arg Cys Leu Glu
705                 710                 715                 720
Gly Glu Val Asp Cys Trp Pro Leu Thr Cys Pro Asn Leu Ser Cys Glu
                725                 730                 735
Tyr Thr Ala Ile Leu Glu Gly Glu Cys Cys Pro Arg Cys Val Ser Asp
```

|     |     |     |     |     |     |     |     |     |     |     |     |
|-----|-----|-----|-----|-----|-----|-----|-----|-----|-----|-----|-----|
|     | 740 |     |     |     | 745 |     |     |     | 750 |     |     |
| Pro | Cys | Leu | Ala | Asp | Asn | Ile | Thr | Tyr | Asp | Ile | Arg | Lys | Thr | Cys | Leu |
|     |     | 755 |     |     |     |     | 760 |     |     |     |     | 765 |     |     |     |
| Asp | Ser | Tyr | Gly | Val | Ser | Arg | Leu | Ser | Gly | Ser | Val | Trp | Thr | Met | Ala |
|     | 770 |     |     |     |     | 775 |     |     |     |     | 780 |     |     |     |     |
| Gly | Ser | Pro | Cys | Thr | Thr | Cys | Lys | Cys | Lys | Asn | Gly | Arg | Val | Cys | Cys |
| 785 |     |     |     |     | 790 |     |     |     |     | 795 |     |     |     |     | 800 |
| Ser | Val | Asp | Phe | Glu | Cys | Leu | Gln | Asn | Asn |
|     |     |     |     | 805 |     |     |     |     | 810 |

<210> SEQ ID NO 2
<211> LENGTH: 2966
<212> TYPE: DNA
<213> ORGANISM: Homo sapiens

<400> SEQUENCE: 2

```
ggcgctgccg agccacctcc cccgccgccc gctagcaagt ttggcggctc caagccaggc      60
gcgcctcagg atccaggctc atttgcttcc acctagcttc ggtgccccct gctaggcggg     120
gaccctcgag agcgatgccg atggatttga ttttagttgt gtggttctgt gtgtgcactg     180
ccaggacagt ggtgggcttt gggatggacc ctgaccttca gatggatatc gtcaccgagc     240
ttgaccttgt gaacaccacc cttggagttg ctcaggtgtc tggaatgcac aatgccagca     300
aagcatttt atttcaagac atagaaagag agatccatgc agctcctcat gtgagtgaga     360
aattaattca gctgttccag aacaagagtg aattcaccat tttggccact gtacagcaga     420
tggagagcag tggcctgagg gatgagattc ggtatcacta catacacaat gggaagccaa     480
ggacagaggc acttccttac cgcatggcag atggacaatg cacaaggtt gcactgtcag     540
ttagcgcctc tcatctcctg ctccatgtcg actgtaacag gatttatgag cgtgtgatag     600
accctccaga taccaacctt cccccaggaa tcaatttatg gcttggccag cgcaaccaaa     660
agcatggctt attcaaaggg atcatccaag atgggaagat catctttatg ccgaatggat     720
atataacaca gtgtccaaat ctaaatcaca cttgcccaac ctgcagtgat tcttaagcc      780
tggtgcaagg aataatggat ttacaagagc ttttggccaa gatgactgca aaactaaatt     840
atgcagagac aagacttagt caattggaaa actgtcattg tgagaagact tgtcaagtga     900
gtggactgct ctatcgagat caagactctt gggtagatgg tgaccattgc aggaactgca     960
cttgcaaaag tggtgccgtg aatgccgaa ggatgtcctg tccccctctc aattgctccc    1020
cagactccct cccagtgcac attgctggcc agtgctgtaa ggtctgccga ccaaaatgta    1080
tctatggagg aaaagttctt gcagaaggcc agcggatttt aaccaagagc tgtcgggaat    1140
gccgaggtgg agtttagta aaaattacag aaatgtgtcc tcctttgaac tgctcagaaa    1200
aggatcacat tcttcctgag aatcagtgct gccgtgtctg tagaggtcat aacttttgtg    1260
cagaaggacc taaatgtggt gaaaactcag agtgcaaaaa ctggaataca aaagctactt    1320
gtgagtgcaa gagtggttac atctctgtcc agggagactc tgcctactgt gaagatattg    1380
atgagtgtgc agctaagatg cattactgtc atgccaatac tgtgtgtgtc aaccttcctg    1440
ggttatatcg ctgtgactgt gtcccaggat acattcgtgt ggatgacttc tcttgtacag    1500
aaacacgatga atgtggcagc ggccagcaca actgtgatga atgccatctg caccaaca     1560
ctgtccaggg acacagctgc acctgcaaac cgggctacgt ggggaacggg accatctgca    1620
gagctttctg tgaagagggc tgcagatacg gtggaacgtg tgtggctccc aacaaatgtg    1680
tctgtccatc tggattcaca ggaagccact gcgagaaaga tattgatgaa tgttcagagg    1740
```

```
gaatcattga gtgccacaac cattcccgct gcgttaacct gccagggtgg taccactgtg    1800
agtgcagaag cggtttccat gacgatggga cctattcact gtccgggag tcctgtattg    1860 acattgatga atgtgcctta agaactcaca cctgttggaa cgattctgcc tgcatcaacc    1920
tggcaggggg ttttgactgt ctctgcccct ctgggccctc ctgctctggt gactgtcctc    1980 atgaagggg gctgaagcac aatggccagg tgtggacctt gaaagaagac aggtgttctg    2040
tctgctcctg caaggatggc aagatattct gccgacggac agcttgtgat tgccagaatc    2100
caagtgctga cctattctgt tgcccagaat gtgacaccag agtcacaagt caatgtttag    2160
accaaaatgg tcacaagctg tatcgaagtg gagacaattg acccatagc tgtcagcagt    2220 gtcggtgtct ggaaggagag gtagattgct ggccactcac ttgccccaac ttgagctgtg    2280
agtatacagc tatcttagaa ggggaatgtt gtccccgctg tgtcagtgac ccctgcctag    2340
ctgataacat cacctatgac atcagaaaaa cttgcctgga cagctatggt gtttcacggc    2400
ttagtggctc agtgtggacg atggctggat ctccctgcac aacctgtaaa tgcaagaatg    2460
gaagagtctg ttgttctgtg gattttgagt gtcttcaaaa taattgaagt atttacagtg    2520
gactcaacgc agaagaatgg acgaaatgac catccaacgt gattaaggat aggaatcggt    2580
agtttggttt ttttgtttgt tttgttttt taaccacaga taattgccaa gtttccacc    2640 tgaggacggt gtttggaggt tgccttttgg acctaccact ttgctcattc ttgctaacct    2700
agtctaggtg acctacagtg ccgtgcattt aagtcaatgg ttgttaaaag aagtttcccg    2760
tgttgtaaat catgtttccc ttatcagatc atttgcaaat acatttaaat gatctcatgg    2820
taaatgttga tgtatttttt ggtttatttt gtgtactaac ataatagaga gagactcagc    2880
tccttttatt tattttgttg atttatggat caaattctaa aataaagttg cctgttgtga    2940
aaaaaaaaaa aaaaaaaaaa aaaaaa                                          2966
```

<210> SEQ ID NO 3
<211> LENGTH: 810
<212> TYPE: PRT
<213> ORGANISM: Rattus norvegicus

<400> SEQUENCE: 3

```
Met Pro Met Asp Val Ile Leu Val Leu Trp Phe Cys Val Cys Thr Ala
1               5                   10                  15

Arg Thr Val Leu Gly Phe Gly Met Asp Pro Asp Leu Gln Leu Asp Ile
                20                  25                  30

Ile Ser Glu Leu Asp Leu Val Asn Thr Thr Leu Gly Val Thr Gln Val
            35                  40                  45

Ala Gly Leu His Asn Ala Ser Lys Ala Phe Leu Phe Gln Asp Val Gln
        50                  55                  60

Arg Glu Ile His Ser Ala Pro His Val Ser Glu Lys Leu Ile Gln Leu
65                  70                  75                  80

Phe Arg Asn Lys Ser Glu Phe Thr Phe Leu Ala Thr Val Gln Gln Lys
                85                  90                  95

Pro Ser Thr Ser Gly Val Ile Leu Ser Ile Arg Glu Leu Glu His Ser
                100                 105                 110

Tyr Phe Glu Leu Glu Ser Ser Gly Pro Arg Glu Glu Ile Arg Tyr His
            115                 120                 125

Tyr Ile His Gly Gly Lys Pro Arg Thr Glu Ala Leu Pro Tyr Arg Met
        130                 135                 140

Ala Asp Gly Gln Trp His Lys Val Ala Leu Ser Val Ser Ala Ser His
```

```
            145                 150                 155                 160
Leu Leu Leu His Ile Asp Cys Asn Arg Ile Tyr Glu Arg Val Ile Asp
                165                 170                 175
Pro Pro Glu Thr Asn Leu Pro Pro Gly Ser Asn Leu Trp Leu Gly Gln
                180                 185                 190
Arg Asn Gln Lys His Gly Phe Phe Lys Gly Ile Ile Gln Asp Gly Lys
                195                 200                 205
Ile Ile Phe Met Pro Asn Gly Phe Ile Thr Gln Cys Pro Asn Leu Asn
            210                 215                 220
Arg Thr Cys Pro Thr Cys Ser Asp Phe Leu Ser Leu Val Gln Gly Ile
225                 230                 235                 240
Met Asp Leu Gln Glu Leu Leu Ala Lys Met Thr Ala Lys Leu Asn Tyr
                245                 250                 255
Ala Glu Thr Arg Leu Gly Gln Leu Glu Asn Cys His Cys Glu Lys Thr
                260                 265                 270
Cys Gln Val Ser Gly Leu Leu Tyr Arg Asp Gln Asp Ser Trp Val Asp
                275                 280                 285
Gly Asp Asn Cys Gly Asn Cys Thr Cys Lys Ser Gly Ala Val Glu Cys
            290                 295                 300
Arg Arg Met Ser Cys Pro Pro Leu Asn Cys Ser Pro Asp Ser Leu Pro
305                 310                 315                 320
Val His Ile Ser Gly Gln Cys Cys Lys Val Cys Arg Pro Lys Cys Ile
                325                 330                 335
Tyr Gly Gly Lys Val Leu Ala Glu Gly Gln Arg Ile Leu Thr Lys Thr
                340                 345                 350
Cys Arg Glu Cys Arg Gly Gly Val Leu Val Lys Ile Thr Glu Ala Cys
                355                 360                 365
Pro Pro Leu Asn Cys Ser Ala Lys Asp His Ile Leu Pro Glu Asn Gln
            370                 375                 380
Cys Cys Arg Val Cys Pro Gly His Asn Phe Cys Ala Glu Ala Pro Lys
385                 390                 395                 400
Cys Gly Glu Asn Ser Glu Cys Lys Asn Trp Asn Thr Lys Ala Thr Cys
                405                 410                 415
Glu Cys Lys Asn Gly Tyr Ile Ser Val Gln Gly Asn Ser Ala Tyr Cys
                420                 425                 430
Glu Asp Ile Asp Glu Cys Ala Ala Lys Met His Tyr Cys His Ala Asn
            435                 440                 445
Thr Val Cys Val Asn Leu Pro Gly Leu Tyr Arg Cys Asp Cys Val Pro
450                 455                 460
Gly Tyr Ile Arg Val Asp Asp Phe Ser Cys Thr Glu His Asp Asp Cys
465                 470                 475                 480
Gly Ser Gly Gln His Asn Cys Asp Lys Asn Ala Ile Cys Thr Asn Thr
                485                 490                 495
Val Gln Gly His Ser Cys Thr Cys Gln Pro Gly Tyr Val Gly Asn Gly
                500                 505                 510
Thr Ile Cys Lys Ala Phe Cys Glu Glu Gly Cys Arg Tyr Gly Gly Thr
            515                 520                 525
Cys Val Ala Pro Asn Lys Cys Val Cys Pro Ser Gly Phe Thr Gly Ser
            530                 535                 540
His Cys Glu Lys Asp Ile Asp Glu Cys Ala Glu Gly Phe Val Glu Cys
545                 550                 555                 560
His Asn Tyr Ser Arg Cys Val Asn Leu Pro Gly Trp Tyr His Cys Glu
                565                 570                 575
```

```
Cys Arg Ser Gly Phe His Asp Asp Gly Thr Tyr Ser Leu Ser Gly Glu
            580                 585                 590

Ser Cys Ile Asp Ile Asp Glu Cys Ala Leu Arg Thr His Thr Cys Trp
        595                 600                 605

Asn Asp Ser Ala Cys Ile Asn Leu Ala Gly Gly Phe Asp Cys Leu Cys
    610                 615                 620

Pro Ser Gly Pro Ser Cys Ser Gly Asp Cys Pro His Glu Gly Leu
625             630                 635                 640

Lys His Asn Gly Gln Val Trp Ile Leu Arg Glu Asp Arg Cys Ser Val
            645                 650                 655

Cys Ser Cys Lys Asp Gly Lys Ile Phe Cys Arg Arg Thr Ala Cys Asp
        660                 665                 670

Cys Gln Asn Pro Asn Val Asp Leu Phe Cys Pro Glu Cys Asp Thr
    675                 680                 685

Arg Val Thr Ser Gln Cys Leu Asp Gln Ser Gly Gln Lys Leu Tyr Arg
690                 695                 700

Ser Gly Asp Asn Trp Thr His Ser Cys Gln Gln Cys Arg Cys Leu Glu
705             710                 715                 720

Gly Glu Ala Asp Cys Trp Pro Leu Ala Cys Pro Ser Leu Gly Cys Glu
            725                 730                 735

Tyr Thr Ala Met Phe Glu Gly Glu Cys Cys Pro Arg Cys Val Ser Asp
        740                 745                 750

Pro Cys Leu Ala Gly Asn Ile Ala Tyr Asp Ile Arg Lys Thr Cys Leu
    755                 760                 765

Asp Ser Phe Gly Val Ser Arg Leu Ser Gly Ala Val Trp Thr Met Ala
770                 775                 780

Gly Ser Pro Cys Thr Thr Cys Lys Cys Lys Asn Gly Arg Val Cys Cys
785             790                 795                 800

Ser Val Asp Leu Glu Cys Ile Glu Asn Asn
            805                 810

<210> SEQ ID NO 4
<211> LENGTH: 2915
<212> TYPE: DNA
<213> ORGANISM: Rattus norvegicus

<400> SEQUENCE: 4
aagcactggt tcttgttag cgttggtgcg ccctgcttgg cggggttct ccggagcgat      60 gccgatggat gtgattttag ttttgtggtt ctgtgtatgc accgccagga cagtgttggg    120
ctttgggatg daccctgacc ttcagctgga catcatctca gagctcgacc tggtgaacac    180
caccctggga gtcacgcagg tggctggact gcacaacgcc agtaaagcat ttctatttca    240
agatgtacag agagagatcc attcggcccc tcacgtgagt gagaagctga tccagctatt    300
ccggaataag agcgagttca ccttttttggc tacagtgcag cagaaaccat ccacctcagg    360
ggtgatactg tccatccggg agctggagca cagctatttt gaactggaga gcagtggccc    420
aagagaagag atacgctacc attacataca tggtggaaag cccaggactg aggcccttcc    480
ctaccgcatg gcagacggac aatggcacaa ggtcgcgctg tcagtgagcg cctctcacct    540
cctgctccac atcgactgca ataggattta cgagcgtgtg atagaccctc cggagaccaa    600
ccttcctcca ggaagcaatc tgtggcttgg gcaacgtaac caaaagcatg gctttttcaa    660
aggaatcatc caagatggta agatcatctt catgccgaat ggtttcatca cacagtgtcc    720
caacctcaat cgcacttgcc aacatgcag tgacttcctg agcctggttc aaggaataat    780
```

-continued

```
ggatttgcaa gagcttttgg ccaagatgac tgcaaaactg aattatgcag agacgagact      840
tggtcaactg gaaaattgcc actgtgagaa gacctgccaa gtgagtgggc tgctctacag      900
ggaccaagac tcctgggtgg atggtgacaa ctgtgggaac tgcacgtgca aaagtggtgc      960
cgtggagtgc cgcaggatgt cctgtccccc gctcaactgt tccccggact cacttcctgt     1020
gcacatttcc ggccagtgtt gtaaagtttg cagaccaaaa tgtatctatg gaggaaaagt     1080
tcttgctgag ggccagcgga ttttaaccaa gacctgccgg gaatgtcgag gtggagtctt     1140
ggtaaaaatc acagaagctt gccctccttt gaactgctca gcaaaggatc atattcttcc     1200
agagaatcag tgctgcaggg tctgcccagg tcataacttc tgtgcagaag cacctaagtg     1260
cggagaaaac tcggaatgca aaaattggaa tacaaaagca acctgtgagt gcaagaatgg     1320
atacatctct gtccagggca actctgcata ctgtgaagat attgatgagt gtgcagctaa     1380
aatgcactat tgtcatgcca acaccgtgtg tgtcaacttg ccggggttgt atcgctgtga     1440
ctgcgtccca gggtacatcc gtgtggatga cttctcttgt acggagcatg atgattgtgg     1500
cagcggacaa cacaactgcg acaaaaatgc catctgtacc aacacagtcc agggacacag     1560
ctgcacctgc cagccgggtt acgtgggaaa tggcaccatc tgcaaagcat ctgtgaaga      1620 gggttgcaga tacggaggta cctgtgtggc tcctaacaag tgtgtctgtc cttctggatt     1680
cacgggaagc cactgtgaga agatattga tgaatgcgca gagggattcg ttgaatgcca      1740
caactactcc cgctgtgtta acctgccagg gtggtaccac tgtgagtgca aagcggttt      1800 ccatgacgat gggacctact cactgtccgg ggagtcctgc attgatatcg atgaatgtgc     1860
cttaagaact cacacttgtt ggaatgactc tgcctgcatc aacttagcag gaggatttga     1920
ctgcctgtgt ccctctgggc cctcctgctc tggtgactgt ccccacgaag agggctgaa      1980 gcataatggg caggtgtgga ttctgagaga agacaggtgt tcagtctgtt cctgcaagga     2040
tgggaagata ttctgccggc ggacagcttg tgattgccag aatccaaatg ttgaccttt      2100 ttgctgccca gagtgcgata ccagggtcac cagccaatgt ttagatcaaa gtggacagaa     2160
gctctatcga agtggagaca actgacccca cagctgccag cagtgccgat gtctggaagg     2220
agaggcagac tgctggcctc tggcttgccc tagtttgggc tgtgaataca cagccatgtt     2280
tgaaggggag tgttgtcccc gatgtgtcag tgaccctgc ctggctggta atattgccta      2340
tgacatcaga aaaacttgcc tggacagctt tggtgtttcg aggctgagcg gagccgtgtg     2400
gacaatggct ggatctcctt gtacaacctg caaatgcaag aatgggagag tctgctgctc     2460
tgtggatctg gagtgtattg agaataactg aagattttaa atggactcgt cacgtgagaa     2520
aatgggcaaa atgatcatcc cacctgagga agaaggggg ctgatttctt tttcttttta      2580
accacagtca attaccaaag tctccatctg aggaaggcgt ttggattgcc tttgccactt     2640
tgctcatcct tgctgaccta gtctagatgc ctgcagtacc gtgcatttcg gtcgatggtt     2700
gttgagtctc agtgttgtaa atcgcatttc cctcgtcaga tcatttacag atacatttaa     2760
aggggttcca tgataaatgt taatgtaact tttgtttatt ttgtgtactg acataataga     2820
gacttggcac catttatta ttttctttga tttttggatc aaattctaaa ataaagttg       2880 cctgttgcga aaaaaaaaaa aaaaaaaaaa aaaaa                                 2915
```

<210> SEQ ID NO 5
<211> LENGTH: 810
<212> TYPE: PRT
<213> ORGANISM: Mus musculus -continued

<400> SEQUENCE: 5

```
Met Pro Met Asp Val Ile Leu Val Leu Trp Phe Cys Val Cys Thr Ala
1               5                   10                  15

Arg Thr Val Leu Gly Phe Gly Met Asp Pro Asp Leu Gln Met Asp Ile
            20                  25                  30

Ile Thr Glu Leu Asp Leu Val Asn Thr Thr Leu Gly Val Thr Gln Val
        35                  40                  45

Ala Gly Leu His Asn Ala Ser Lys Ala Phe Leu Phe Gln Asp Val Gln
    50                  55                  60

Arg Glu Ile His Ser Ala Pro His Val Ser Glu Lys Leu Ile Gln Leu
65                  70                  75                  80

Phe Arg Asn Lys Ser Glu Phe Thr Phe Leu Ala Thr Val Gln Gln Lys
                85                  90                  95

Pro Ser Thr Ser Gly Val Ile Leu Ser Ile Arg Glu Leu Glu His Ser
            100                 105                 110

Tyr Phe Glu Leu Glu Ser Ser Gly Pro Arg Glu Glu Ile Arg Tyr His
        115                 120                 125

Tyr Ile His Gly Gly Lys Pro Arg Thr Glu Ala Leu Pro Tyr Arg Met
    130                 135                 140

Ala Asp Gly Gln Trp His Lys Val Ala Leu Ser Val Ser Ala Ser His
145                 150                 155                 160

Leu Leu Leu His Val Asp Cys Asn Arg Ile Tyr Glu Arg Val Ile Asp
                165                 170                 175

Pro Pro Glu Thr Asn Leu Pro Pro Gly Ser Asn Leu Trp Leu Gly Gln
            180                 185                 190

Arg Asn Gln Lys His Gly Phe Phe Lys Gly Ile Ile Gln Asp Gly Lys
        195                 200                 205

Ile Ile Phe Met Pro Asn Gly Phe Ile Thr Gln Cys Pro Asn Leu Asn
    210                 215                 220

Arg Thr Cys Pro Thr Cys Ser Asp Phe Leu Ser Leu Val Gln Gly Ile
225                 230                 235                 240

Met Asp Leu Gln Glu Leu Leu Ala Lys Met Thr Ala Lys Leu Asn Tyr
                245                 250                 255

Ala Glu Thr Arg Leu Gly Gln Leu Glu Asn Cys His Cys Glu Lys Thr
            260                 265                 270

Cys Gln Val Ser Gly Leu Leu Tyr Arg Asp Gln Asp Ser Trp Val Asp
        275                 280                 285

Gly Asp Asn Cys Arg Asn Cys Thr Cys Lys Ser Gly Ala Val Glu Cys
    290                 295                 300

Arg Arg Met Ser Cys Pro Pro Leu Asn Cys Ser Pro Asp Ser Leu Pro
305                 310                 315                 320

Val His Ile Ser Gly Gln Cys Cys Lys Val Cys Arg Pro Lys Cys Ile
                325                 330                 335

Tyr Gly Gly Lys Val Leu Ala Glu Gly Gln Arg Ile Leu Thr Lys Thr
            340                 345                 350

Cys Arg Glu Cys Arg Gly Gly Val Leu Val Lys Ile Thr Glu Ala Cys
        355                 360                 365

Pro Pro Leu Asn Cys Ser Glu Lys Asp His Ile Leu Pro Glu Asn Gln
    370                 375                 380

Cys Cys Arg Val Cys Arg Gly His Asn Phe Cys Ala Glu Ala Pro Lys
385                 390                 395                 400

Cys Gly Glu Asn Ser Glu Cys Lys Asn Trp Asn Thr Lys Ala Thr Cys
                405                 410                 415
```

Glu Cys Lys Asn Gly Tyr Ile Ser Val Gln Gly Asn Ser Ala Tyr Cys
            420                 425                 430

Glu Asp Ile Asp Glu Cys Ala Ala Lys Met His Tyr Cys His Ala Asn
            435                 440                 445

Thr Val Cys Val Asn Leu Pro Gly Leu Tyr Arg Cys Asp Cys Ile Pro
            450                 455                 460

Gly Tyr Ile Arg Val Asp Asp Phe Ser Cys Thr Glu His Asp Asp Cys
465                 470                 475                 480

Gly Ser Gly Gln His Asn Cys Asp Lys Asn Ala Ile Cys Thr Asn Thr
                485                 490                 495

Val Gln Gly His Ser Cys Thr Cys Gln Pro Gly Tyr Val Gly Asn Gly
            500                 505                 510

Thr Val Cys Lys Ala Phe Cys Glu Glu Gly Cys Arg Tyr Gly Gly Thr
            515                 520                 525

Cys Val Ala Pro Asn Lys Cys Val Cys Pro Ser Gly Phe Thr Gly Ser
            530                 535                 540

His Cys Glu Lys Asp Ile Asp Glu Cys Ala Glu Gly Phe Val Glu Cys
545                 550                 555                 560

His Asn His Ser Arg Cys Val Asn Leu Pro Gly Trp Tyr His Cys Glu
                565                 570                 575

Cys Arg Ser Gly Phe His Asp Asp Gly Thr Tyr Ser Leu Ser Gly Glu
            580                 585                 590

Ser Cys Ile Asp Ile Asp Glu Cys Ala Leu Arg Thr His Thr Cys Trp
            595                 600                 605

Asn Asp Ser Ala Cys Ile Asn Leu Ala Gly Gly Phe Asp Cys Leu Cys
            610                 615                 620

Pro Ser Gly Pro Ser Cys Ser Gly Asp Cys Pro His Glu Gly Gly Leu
625                 630                 635                 640

Lys His Asn Gly Gln Val Trp Ile Leu Arg Glu Asp Arg Cys Ser Val
                645                 650                 655

Cys Ser Cys Lys Asp Gly Lys Ile Phe Cys Arg Arg Thr Ala Cys Asp
            660                 665                 670

Cys Gln Asn Pro Asn Val Asp Leu Phe Cys Cys Pro Glu Cys Asp Thr
            675                 680                 685

Arg Val Thr Ser Gln Cys Leu Asp Gln Ser Gly Gln Lys Leu Tyr Arg
            690                 695                 700

Ser Gly Asp Asn Trp Thr His Ser Cys Gln Gln Cys Arg Cys Leu Glu
705                 710                 715                 720

Gly Glu Ala Asp Cys Trp Pro Leu Ala Cys Pro Ser Leu Ser Cys Glu
                725                 730                 735

Tyr Thr Ala Ile Phe Glu Gly Glu Cys Cys Pro Arg Cys Val Ser Asp
            740                 745                 750

Pro Cys Leu Ala Asp Asn Ile Ala Tyr Asp Ile Arg Lys Thr Cys Leu
            755                 760                 765

Asp Ser Ser Gly Ile Ser Arg Leu Ser Gly Ala Val Trp Thr Met Ala
            770                 775                 780

Gly Ser Pro Cys Thr Thr Cys Gln Cys Lys Asn Gly Arg Val Cys Cys
785                 790                 795                 800

Ser Val Asp Leu Val Cys Leu Glu Asn Asn
                805                 810

<210> SEQ ID NO 6
<211> LENGTH: 2752

```
<212> TYPE: DNA
<213> ORGANISM: Mus musculus

<400> SEQUENCE: 6
gcgttggtgc gccctgcttg gcggggggcc tccggagcga tgccgatgga tgtgatttta      60
gttttgtggt tctgtgtgtg caccgccagg acagtgctgg gctttgggat ggaccctgac     120
cttcagatgg acatcatcac tgaacttgac cttgtgaaca ccaccctggg cgtcactcag     180
gtggctggac tacacaatgc cagtaaggca tttctgtttc aagatgtaca gagagagatc     240
cactcagccc ctcatgtgag tgagaagctg atccagctat tccggaataa gagtgagttt     300
accttttttgg ctacagtgca gcagaagccg tccacctcag gggtgatact gtcgatccgg     360
gagctggaac acagctattt tgaactggag agcagtggcc aagagaaga gatacgctat      420
cattacatcc atggcggcaa gcccaggact gaggcccttc cctaccgcat ggccgatgga     480
cagtggcaca aggtcgcgct gtctgtgagc gcctctcacc tcctactcca tgtcgactgc     540
aataggattt atgagcgtgt gatagatcct ccggagacca accttcctcc aggaagcaat     600
aagatcatct tcatgccgaa cggcttcatc acacagtgcc ccaacctaaa tcgcacttgc     660
ccaacatgca gtgatttcct gagcctggtt caaggaataa tggatttgca agagcttttg     720
gccaagatga ctgcaaaact gaattatgca gagacgagac ttggtcaact ggaaaattgc     780
cactgtgaga agacctgcca agtgagtggg ctgctctaca gggaccaaga ctcctgggta     840
gatggtgaca actgcaggaa ctgcacatgc aaaagtggtg ctgtggagtg ccgaaggatg     900
tcctgtcccc cactcaactg ttccccagac tcacttcctg tgcatatttc tggccaatgt     960
tgtaaagttt gcagaccaaa atgtatctat ggaggaaaag ttcttgctga gggccagcgg    1020
attttaacca agacctgccg ggaatgtcga ggtggagtct tggtaaaaat cacagaagct    1080
tgccctcctt tgaactgctc agagaaggat catattcttc cggagaacca gtgctgcagg    1140
gtctgccgag gtcataactt ctgtgcagaa gcacctaagt gtggagaaaa ctcggaatgc    1200
aaaaattgga atacaaaagc gacttgtgag tgcaagaatg gatacatctc tgtccagggc    1260
aactctgcat actgtgaaga tatcgatgag tgtgcagcaa agatgcacta ctgtcatgcc    1320
aacacggtgt gtgtcaactt gccggggtta tatcgctgtg actgcatccc aggatacatc    1380
cgtgtggatg acttctcttg tacggagcat gatgattgtg gcagcggaca acacaactgt    1440
gacaaaaatg ccatctgtac caacacagtc cagggacaca gctgtacctg ccagccaggc    1500
tacgtgggaa atggtactgt ctgcaaagca ttctgtgaag agggttgcag atacggaggt    1560
acctgtgtgg cccctaacaa atgtgtctgt ccttctggat tcacaggaag ccactgtgag    1620
aaagatattg atgaatgtgc agagggattc gttgagtgcc acaaccactc ccgctgcgtt    1680
aaccttccag ggtggtacca ctgtgagtgc agaagcggtt ccatgacga tgggacctat    1740
tcactgtccg gggagtcctg cattgatatt gatgaatgtg ccttaagaac tcacacttgt    1800
tggaatgact ctgcctgcat caacttagca ggaggatttg actgcctgtg tccctctggg    1860
ccctcctgct ctggtgactg tccccacgaa gggggggctga agcataatgg gcaggtgtgg    1920
attctgagag aagacaggtg ttcagtctgt tcctgtaagg atgggaagat attctgccgg    1980
cggacagctt gtgattgcca gaatccaaat gttgaccttt tctgctgccc agagtgtgac    2040
accagggtca ctagccaatg tttagatcaa agcggacaga agctctatcg aagtggagac    2100
aactggaccc cagctgccca gcagtgccga tgtctggaag gagaggcaga ctgctggcct    2160
ctagcttgcc ctagtttgag ctgtgaatac acagccatct ttgaaggaga gtgttgtccc    2220
```

```
cgctgtgtca gtgaccoctg cctggctgat aatattgcct atgacatcag aaaaacttgc    2280
ctggacagct ctggtatttc gaggctgagc ggcgcagtgt ggacaatggc tggatctccc    2340
tgtacaacct gtcaatgcaa gaatgggaga gtctgctgct ctgtggatct ggtgtgtctt    2400
gagaataact gaagatttta aatggactca tcacatgaga aaatggacaa aatgaccatc    2460
caacctgagg aagaggaggg gctgatttct ttttctttt  aaccacagtc aattaccaaa    2520
gtctccatca gaggaaggcg tttgggttgc ctttaccact ttgctcatcc ttgctgacct    2580
agtctagatg cctgcagtac cgtgtatttc ggtcgatggt tgttgagtct ccgtgctgta    2640
aatcacattt cccttgtcag atcatttaca gatacattta aaggattcca tgataaatgt    2700
taaagtacct tttgtttatt ttgtgtacca acataataga gacttggcac ca            2752
```